(12) United States Patent
Lee et al.

(10) Patent No.: US 10,046,001 B2
(45) Date of Patent: Aug. 14, 2018

(54) COMPOSITIONS AND METHODS FOR REDUCING INTRAOCULAR PRESSURE

(71) Applicant: UNIVERSITY OF MIAMI, Miami, FL (US)

(72) Inventors: Richard K. Lee, Miami, FL (US); Sanjoy K. Bhattacharya, North Bay Village, FL (US)

(73) Assignee: UNIVERSITY OF MIAMI, Miami, FL (US)

( * ) Notice: Subject to any disclaimer, the term of this patent is extended or adjusted under 35 U.S.C. 154(b) by 10 days.

(21) Appl. No.: 15/102,201

(22) PCT Filed: Dec. 4, 2014

(86) PCT No.: PCT/US2014/068671
§ 371 (c)(1),
(2) Date: Jun. 6, 2016

(87) PCT Pub. No.: WO2015/085121
PCT Pub. Date: Jun. 11, 2015

(65) Prior Publication Data
US 2016/0339043 A1    Nov. 24, 2016

Related U.S. Application Data

(60) Provisional application No. 61/912,070, filed on Dec. 5, 2013.

(51) Int. Cl.
| | |
|---|---|
| A61K 9/48 | (2006.01) |
| A61K 31/683 | (2006.01) |
| A61K 31/557 | (2006.01) |
| A61K 31/685 | (2006.01) |
| A61K 31/688 | (2006.01) |
| A61K 31/661 | (2006.01) |
| A61K 31/675 | (2006.01) |
| A61K 9/00 | (2006.01) |
| A61K 47/20 | (2006.01) |
| A61K 45/06 | (2006.01) |
| A61K 47/10 | (2017.01) |
| A61K 47/22 | (2006.01) |
| A61K 47/24 | (2006.01) |

(52) U.S. Cl.
CPC .......... *A61K 31/675* (2013.01); *A61K 9/0048* (2013.01); *A61K 31/557* (2013.01); *A61K 31/661* (2013.01); *A61K 31/683* (2013.01); *A61K 31/685* (2013.01); *A61K 31/688* (2013.01); *A61K 45/06* (2013.01); *A61K 47/20* (2013.01); *A61K 47/10* (2013.01); *A61K 47/22* (2013.01); *A61K 47/24* (2013.01)

(58) Field of Classification Search
CPC ...... A61K 9/48; A61K 31/683; A61K 31/557; A61K 31/685; A61K 31/688; A61K 31/661
See application file for complete search history.

(56) References Cited

U.S. PATENT DOCUMENTS

| | | | |
|---|---|---|---|
| 2008/0182902 A1* | 7/2008 | Nieuwenhuizen | A23J 7/00 514/560 |
| 2011/0294730 A1 | 12/2011 | Shantha et al. | |
| 2013/0267591 A1 | 10/2013 | Khopade et al. | |
| 2013/0295075 A1 | 11/2013 | Hill | |
| 2013/0310370 A1 | 11/2013 | Mizuno | |

FOREIGN PATENT DOCUMENTS

WO    WO-2000/04898 A1    2/2000

OTHER PUBLICATIONS

Dvoriatchikova et at. "Phosphatidylserine-contaning liposomes promote maximal survival of retinal neurons after ischemic injury" Journal of Cerebral Blood Flow & Metabolism, 2009, vol. 29, pp. 1755-1759.*
Wang et al. "Increased Expression of Serum Amyloid A in Glaucoma and Its Effect on Intraocular Pressure" Investigative Opthalmology & Visual Science, 2008, vol. 49, No. 5, pp. 1916-1923.*
Ma et al. "Intraocular Expression of Serum Amyloid A and Intraleukin-6 in Proliferative Diabetic Retinopathy" Am J Ophthalmol, 2011, vol. 152, pp. 678-685.*
Aljohani et al., Sphingolipids and cerarnides in human aqueous humor, *Molecular Vision*, 19: 1966-84 (2013).
Goel et al., Aqueous humor dynamics: a review, *Open Ophthalmol.*, 4:52-9 (2010).
Ilagan et al., Linear measurement of cell contraction in a capillary collagen gel system. *Biotechniques*, 48:153-5 (2010).
Russell et al., Elastic Modulus Determination of Normal and Glaucomatous Human Trabecular Meshwork, *Invest Ophthalmol Vis Sci.*, 53: 117 (2012).
International Search Report and Written Opinion of the International Search Authority, United States Patent and Trademark Office, PCT/US14/68671 dated Dec. 5, 2013.
International Preliminary Report on Patentability, PCT/US2014/068671 dated Jun. 7, 2016.

* cited by examiner

*Primary Examiner* — Kendra D Carter
(74) *Attorney, Agent, or Firm* — Marshall, Gerstein & Borun LLP

(57) ABSTRACT

Compositions, kits, and methods for reducing intraocular pressure (IOP) in a subject (e.g., human) include at least one naturally occurring or synthesized version or analog thereof of a lipid (e.g., a phosphoserine, a phosphocholine, a psychosine or other glycolipid) that is endogenous to non-glaucomatous aqueous humor in a subject and that lowers IOP in the subject, in a therapeutically effective amount for promoting aqueous outflow through TM in at least one eye of the subject and reducing IOP in the subject. The compositions can be used for, e.g., treating glaucomas, including, for example, primary open angle glaucoma (POAG) and normal tension glaucoma (NTG).

9 Claims, 16 Drawing Sheets

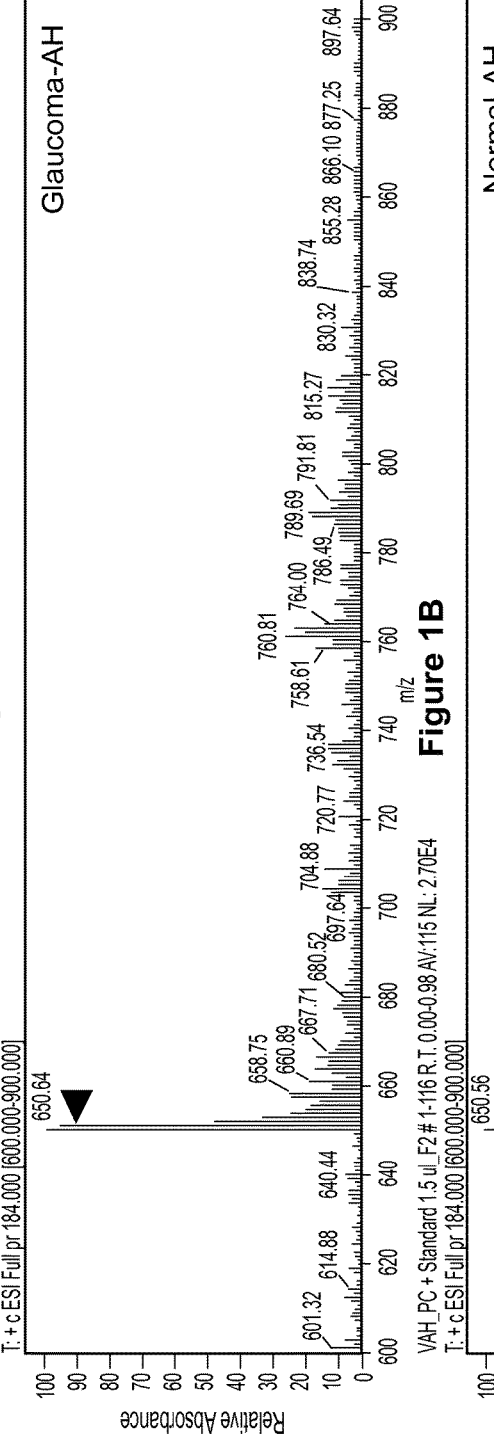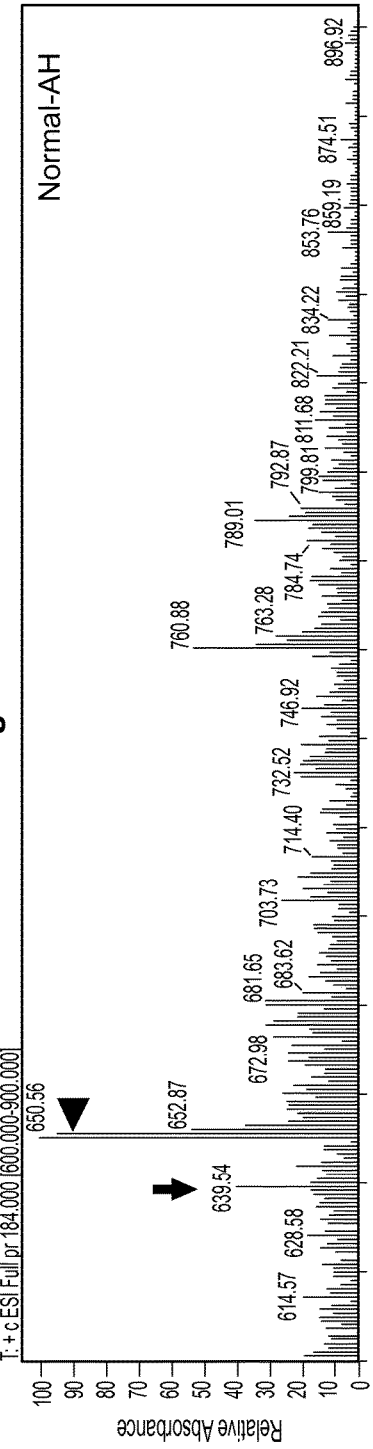

Figure 1. Representative mass spectrometric data demonstrating disappearance of a phosphatidylcholine (PC) species in Glaucomatous aqueous humor (AH) compared to normal control AH. Electrospray ionization mass spectrometric analysis of PC class of lipids in human AH in positive-ion mode. A. and B. are representative analysis of human glaucomatous and normal AH as indicated with internal standard (arrowhead; m/z ratio of 650.6) was used for ratiometric quantification. Parent ion scan was performed for m/z 600-900. Arrow shows presence of a unique species in normal AH.

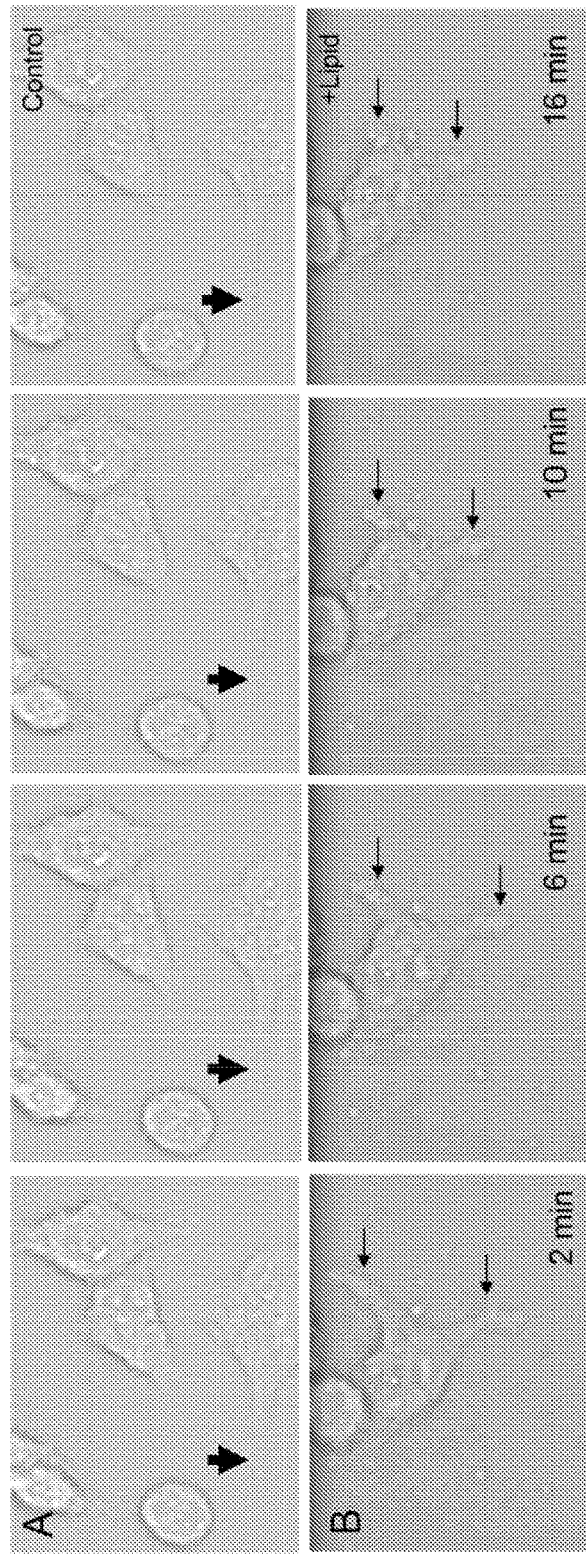

Figure 2. Representative images of effect of lipid on trabecular meshwork primary cells. The time lapsed images of cell at indicated time interval. A. The control TM cells were subjected to vehicle (5% DMSO) in phosphate buffered saline. Most cells in the control group remain rounded or only somewhat elongated with a few that showed having a protrusion. A protrusion of filopodia in a cell is indicated by thick arrow head. At 2 minutes after addition of vehicle to 16 minutes, the protrusion remains unchanged. B. TM cells treated with 10 pmoles of lipid. Most cells have protrusions with only a few cells without them. The filopodia in lipid treated cells are dynamic, they undergo dynamic retraction starting at 1 or 2 minutes after addition of lipid in the serum free media, indicated by arrows. At 16 minutes filopodia are largely retracted.

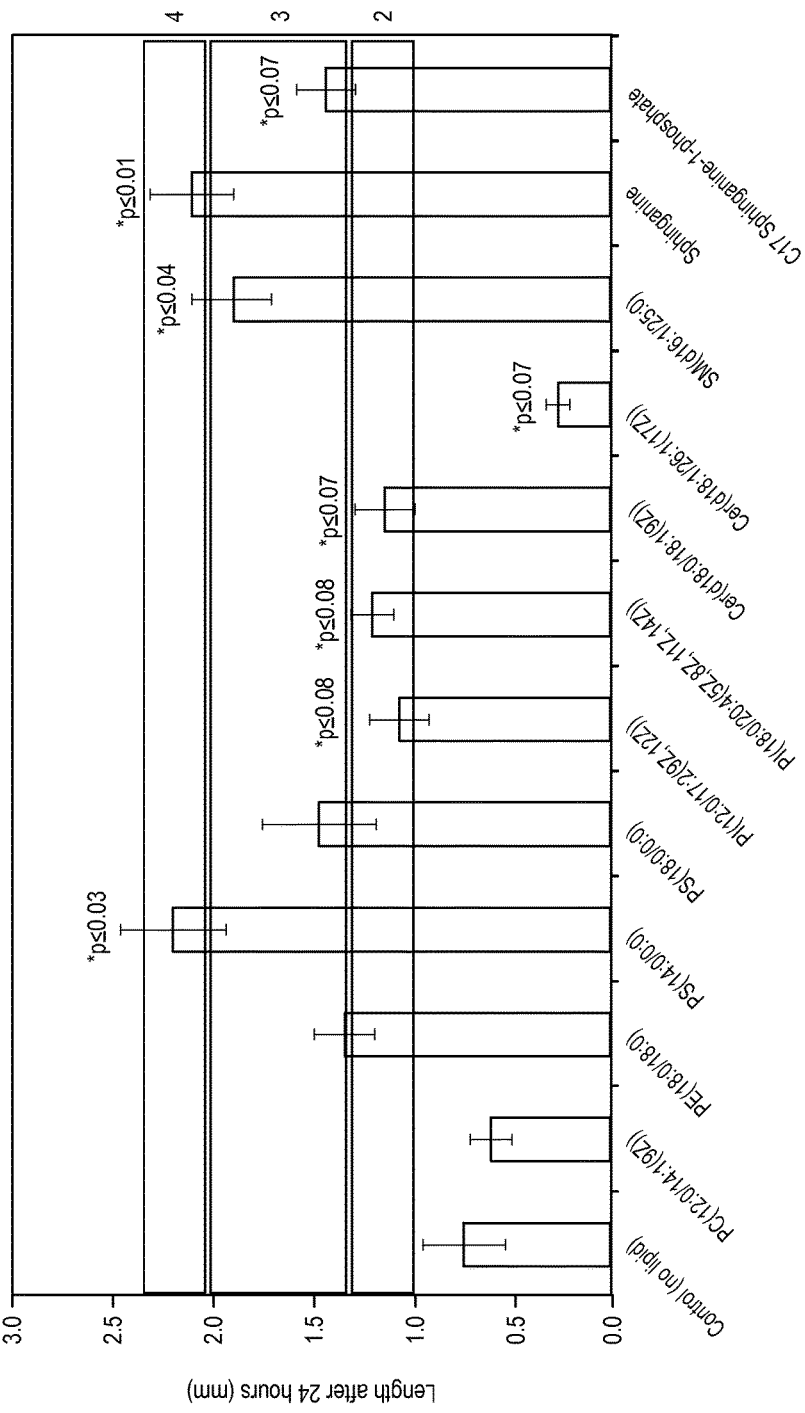

Figure 3

The Collagen gel embedded expansion and/or contraction assay. About 10,000 primary TM cells were placed in a capillary tube with rat collagen without (control) or after treatment with 10 pmole of indicated lipid. The change in collagen column length was measured at the end of 24 hours. Mean and standard deviation from three independent experiments have been presented. As shown by yellow zones, the expansions were categorized into four zones (2, 3 and 4 are identified in blue), 1= > 1.0 mm; 2= 1.0 to 1.4 mm; 3= >1.4 mm but <2.0 mm; 4= 2.0 and >2.0 mm.

Figure 4

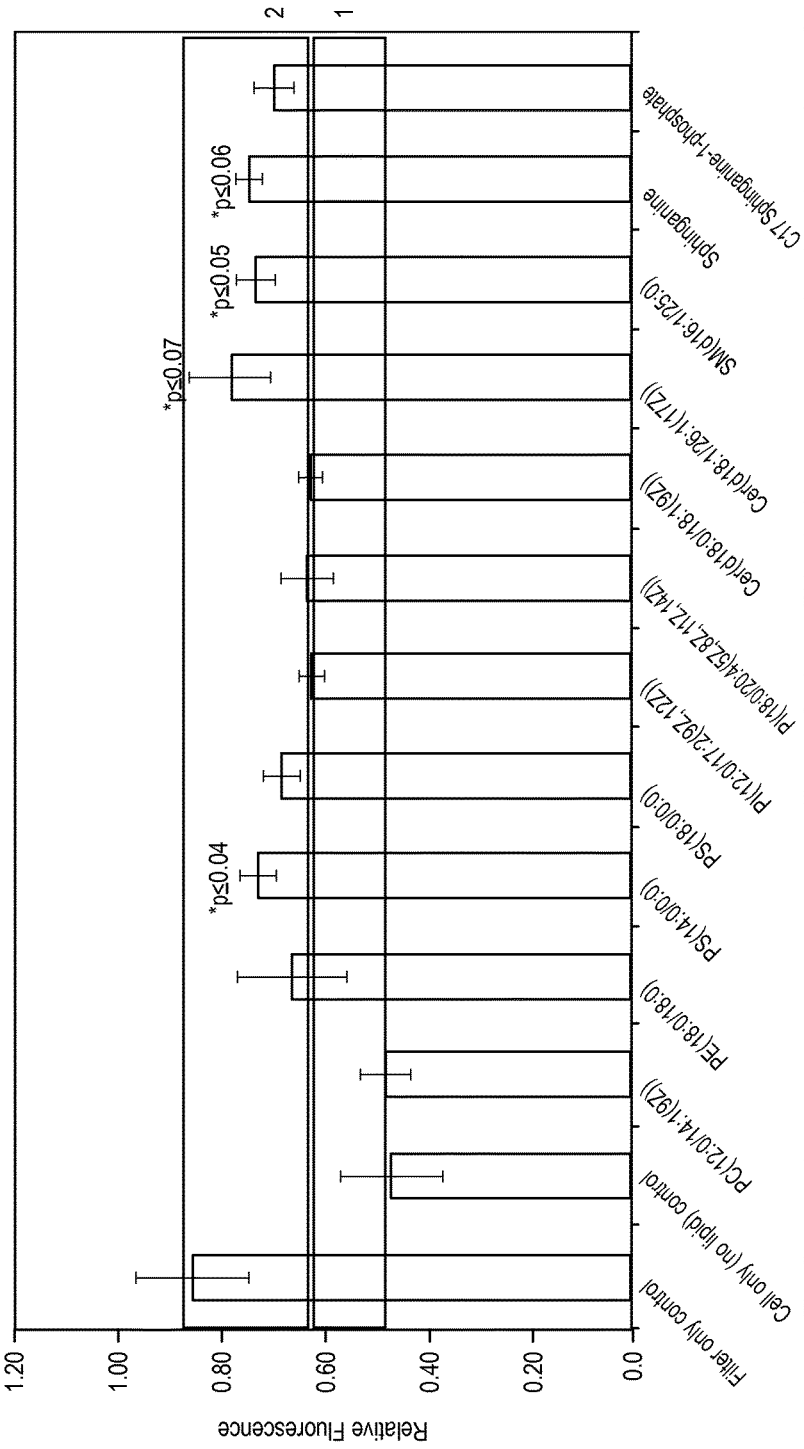

The fluorescein transport assay across a multilayer of primary TM cells in a Ussing type chamber. A pentalayer of cells were casted on a PVDF filter of 0.45μm pore size with second to fourth layer topped with rat collagen. Control (without lipid treatment) or with 10 pmole of indicated lipid treated cells were used for these measurements. The transport of flourescein at 15 seconds from the opposite end after introduction of sample at one was estimated. Mean and standard deviation from three independent experiments have been presented. The relative transport has been divided into two zones (marked in yellow), that when the transport is above 0.48 but less than 0.62 = 1; and above 0.62= 2 as indicated.

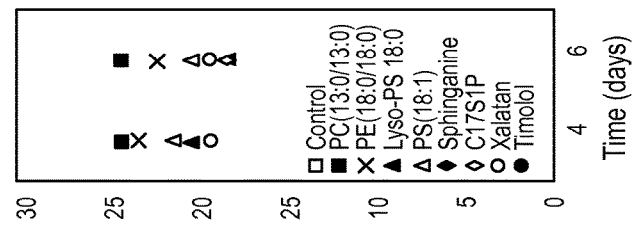
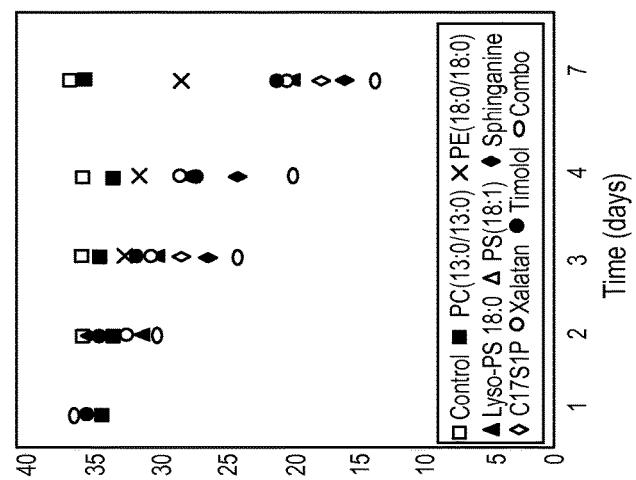
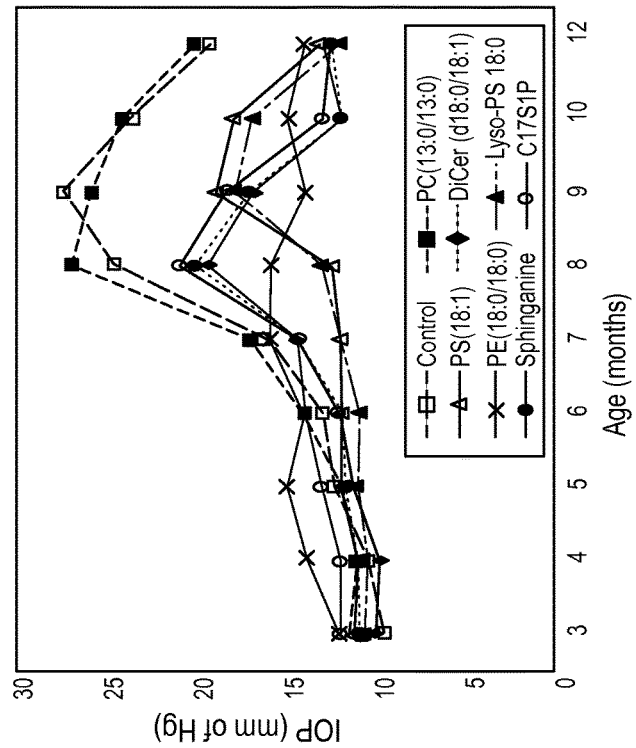

Measurement of intraocular pressure in mice using topical application of 10 pmole of indicated lipid in 5% DMSO (vehicle) in 1 µl administered during 1-4 pm in the afternoon. The right eye was treated with vehicle alone and left eye treated with lipid. Control had both eyes treated with vehicle. A. In DBA/2J mice the indicated lipid in vehicle or control (vehicle only) were administered one daily at around 7.5 months of age in mice which were noted to have a IOP ≥18 mm of Hg (we used a 20% increase from an average baseline of 15 mm of Hg as treatment point). The average IOP recording are being shown for indicated lipids. B. The indicated lipids were topically administered in selected mice (n= 5) and representative figure is shown in mice whose IOP was considerable elevated (~35 mm of Hg). Combo refers to combination of 10 pmole of each of the following six lipids: PC (13:0/13:0); PE (18:0/18:0); Lyso-PS 18:0, PS 18:1, Sphinganine and C17S1P. C. Transgenic myocillin mice [Tg-MYOC(Y437H)] subjected to topical dose of indicated lipids as noted above. The IOP lowering compared to control was noted on day 4 and 6 as shown.

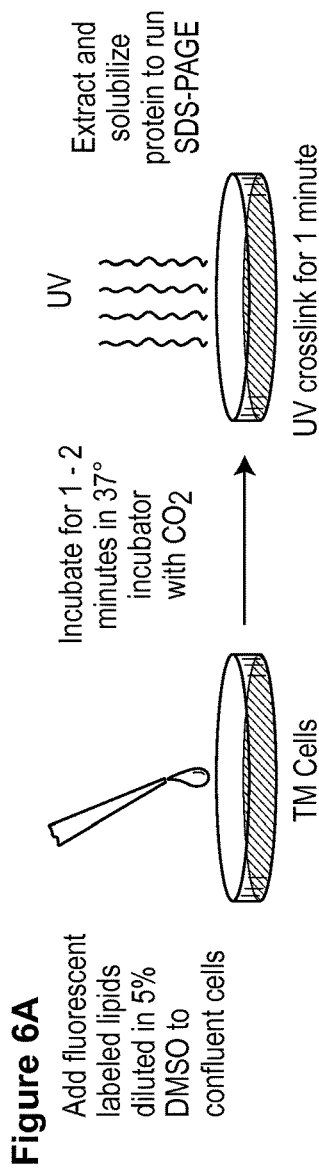
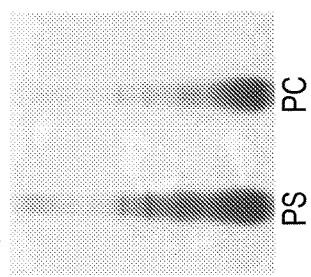
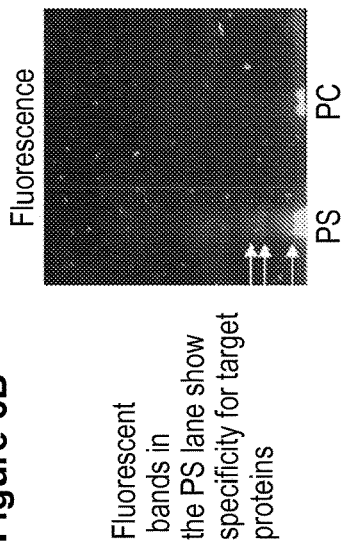

Figure 6A
Add fluorescent labeled lipids diluted in 5% DMSO to confluent cells

Figure 6B
Fluorescent bands in the PS lane show specificity for target proteins

Figure 6C
Coomassie blue

Approach to identify protein targets of lipids. A. The 10 pmole of identified lipid in 5% DMSO (vehicle) was applied on to 40% confluent primary TM cells and after incubation of 1 minute subjected to UV cross linking in a UV Stratalinker 1800 cross-linker for about 1 minute. B. The cells were subjected to lysis with 1% SDS and protein extracts were fractionated over a 4-20% gradient SDS-PAGE. C. The same SDS-PAGE stained with Coommassie blue.

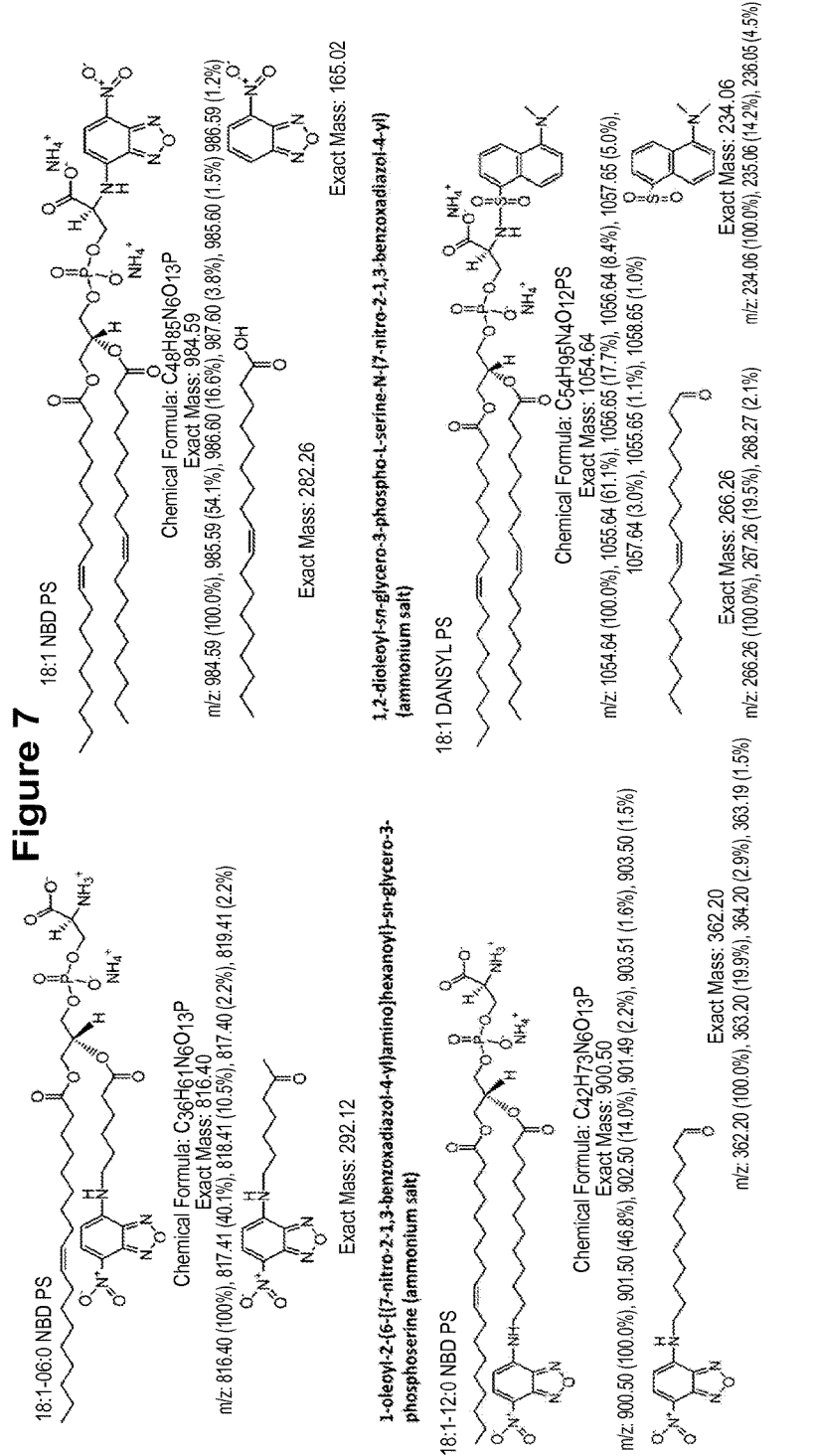

Identification of channels in the human TM derived primary cells. About 11 of these channels were initially identified as cross-linked protein to one or more lipids within first 2 minutes of incubation of TM cells with PS (18: 1) lipid analogs.

Identification of channels in the human TM derived primary cells. About 11 of these channels were initially identified as cross-linked protein to one or more lipids within first 2 minutes of incubation of TM cells with PS (18: 1) lipid analogs.

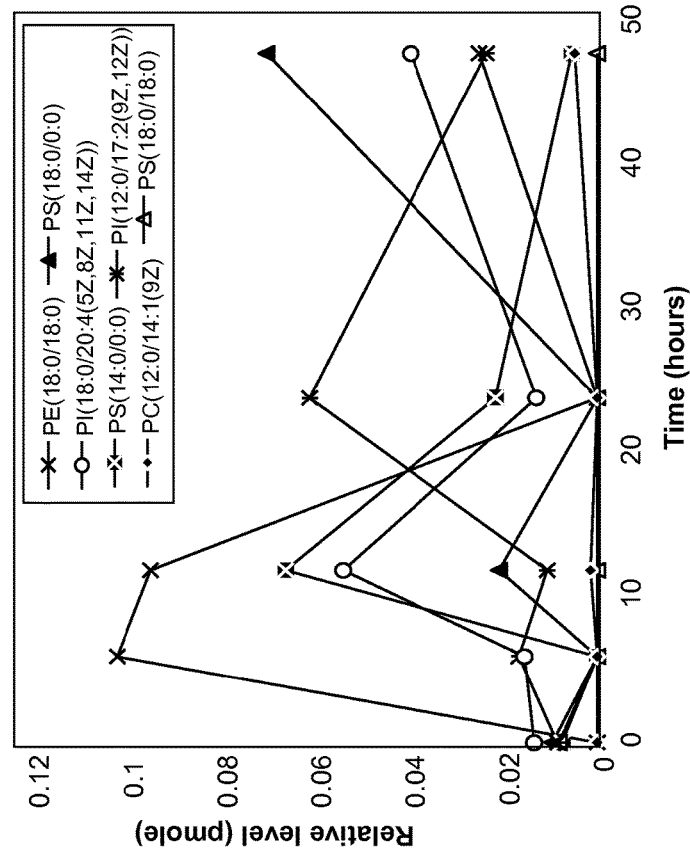
Figure 9C
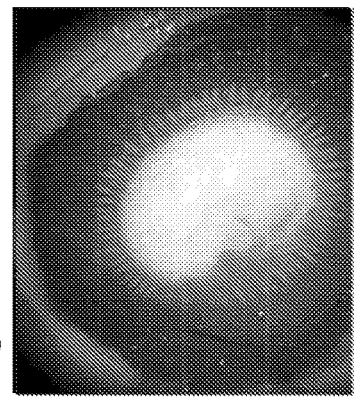
Figure 9A Inside view
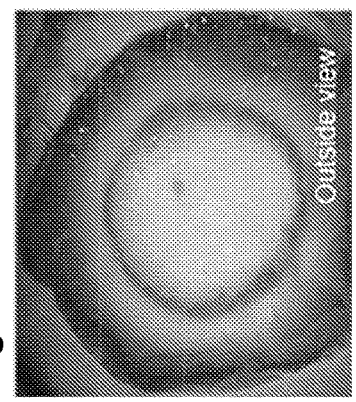
Figure 9B Outside view
Lipid production in mixed culture of ciliary body. A. The organ culture of ciliary body (CB) after enucleation, excision and thorough washing, the CB was placed in serum free medium. B. The outside view of the same CB as in A. C. Detection of lipids at time interval in the serum free medium at indicated time point.

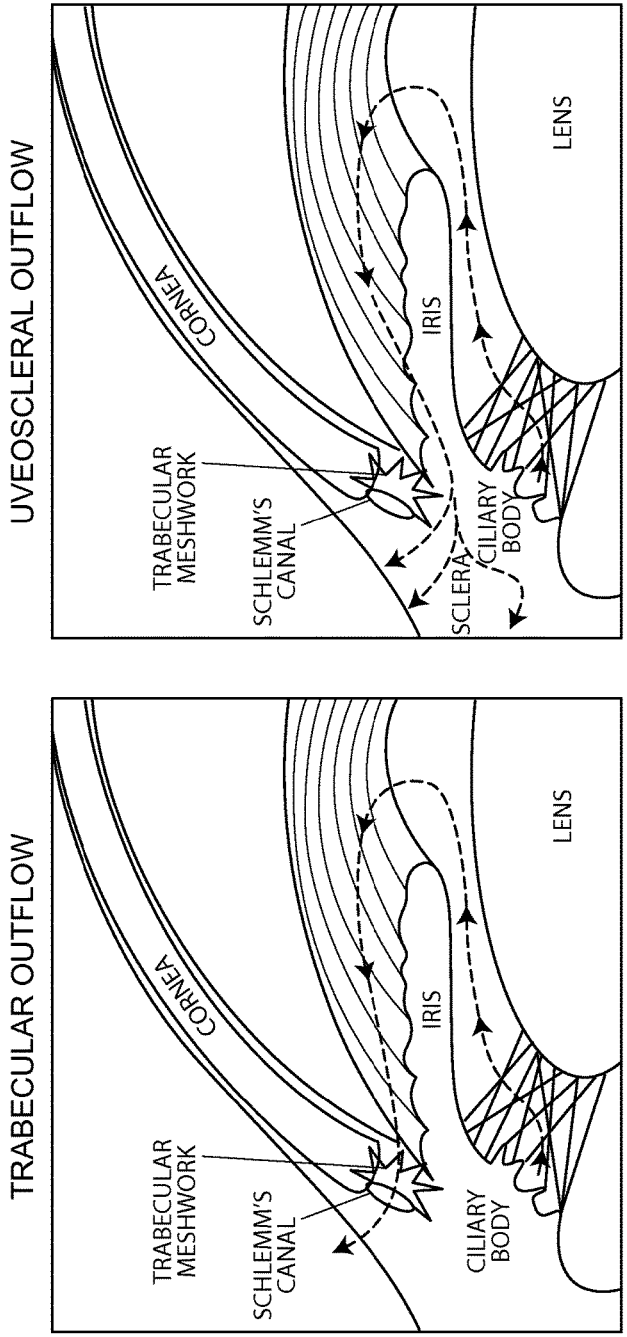

Figure 10A Figure 10B

A schematic diagram of the anterior chamber of the eye depicting A. conventional or trabecular meshwork mediated and B. uveoscleral pathway. The prostanoids increase uveoscleral outflow whereas the mechanosensing protein interactors of our identified lipids resides in the conventional pathway and hence we expect these endogenous lipids will enhance conventional outflow towards lowering IOP. [Adopted from Goel et al (2010). PMID: 21293732].

Figure 11

| | m/z | | Description | Amount* | Effect on IOP (DBA/2J mice) | Effect on Cells** (enhanced mobility) | Effect on gel expansion† | Effect on transport†† | Effect on elastic Modulus | Composite Index (Max= 10) |
|---|---|---|---|---|---|---|---|---|---|---|
| | | | Phosphatidylcholines | | | | | | | |
| 1 | 646.6334 | PC(12:0/14:1) | PC(12:0/14:1(9Z)) | 9.84 | Not available | (1) | (1) | No effect | NA | 2 |
| 2 | 649.90 | PC(13:0/13:0) | 1,2-ditridecanoyl-sn-glycero-3-phosphocholine PC(13:0/13:0) | | No effect * | No effect | No effect | No effect | NA | |
| | | | Phosphatidylethanolamines | | | | | | | |
| 3 | 750.4638 | PE(18:0/18:0) | PE(18:0/18:0) (1,2-dioctadecanoyl-sn-glycero-3-phosphoethanolamine) | 65.8 (123.72) | IOP lowering | (2) | (2) | (2) | NA | 6 |
| | | | Phosphatidylserines | | | | | | | |
| 4 | 468.0331 | PS(14:0/0:0) | PS(14:0/0:0) | 23.10 | Not available | (3) | (4) | (2) | NA | 9 |
| 5 | 791.5676 | PS(18:0/0:0) | PS(18:0/0:0) | | Not available | (3) | (3) | (2) | NA | 8 |
| 6 | 547.60 | Lyso-PS 18:0 | 1-octadecanoyl-sn-glycero-3-phospho-L-serine (sodium salt) (18:0) Lyso-PS | | IOP lowering | (3) | (4) | (2) | NA | 9 |
| 7 | 810.03 | PS (18:1) | 1,2-dioleoyl-sn-glycero-3-phospho-L-serine (sodium salt) 18:1 PS | | IOP lowering | (3) | (4) | (2) | NA | 9 |
| 8 | 762.6639 | PI(12:0/17:2) | PI(12:0/17:2(9Z,12Z)) | 24.33 | Not attempted | (2) | (2) | (1) | NA | 5 |
| 9 | 886.0717 | PI(18:0/20:4) | PI(18:0/20:4(5Z,8Z,11Z,14Z)) | 527.54 | Not attempted | (2) | (2) | (1) | NA | 5 |
| | | | Ceramides | | | | | | | |
| 10 | 568.7258 | Cer(d18:0/18:1) | Cer(d18:0/18:1(9Z)) | 2.44 (68.16) | Not available | (2) | (2) | (1) | NA | 5 |
| 11 | 566.00 | DiCer(d18:0/18:1) | C18:1 Dihydroceramide (d18:0/18:1(9Z)) (N-oleoyl-D-erythro-sphinganine) | | IOP lowering | (4) | (2) | (2) | NA | 8 |
| 12 | 679.2484 | Cer(d18:1/26:1) | Cer(d18:1/26:1(17Z)) | 71.38 | Not attempted | (2) | (1) | (2) | NA | 5 |
| 13 | 804.5194 | SM(d16:1/25:0) | SM(d16:1/25:0) | 69.22 | Not attempted | (4) | (3) | (2) | NA | 9 |
| | | | Sphingoid base | | | | | | | |
| 14 | 303.4092 | Sphinganine | C17 Sphinganine | 0.03 (0.07) | IOP lowering | (4) | (4) | (2) | NA | 10 |
| | | | Sphinganine-1-phosphate | | | | | | | |
| 15 | 367.2488 | C17 Sphinganine1P | C17 Sphinganine-1-phosphate | 0.03 (0.07) | IOP lowering | (3) | (3) | (2) | NA | 8 |

*Amount refers to protein normalized lipid amount (pmole lipid/μg protein). Male amounts follows female amounts, later is presented in parenthesis. **Enhanced mobility: 1 least and 4 most. Gel expansion in mm over control. †1= > 1.0 mm; 2= 1.0 to 1.4 mm; 3= >1.4 mm but <2.0 mm; 4= 2.0 and >2.0 mm. ††Above 0.48= 1; above 0.62= 2. [Note red denotes compounds where synthetic purified compounds are not commercially available. A small scale synthesized products were evaluated on cells but not in vivo. The bold molecules are commercially structural analogs and were evaluated. The PC 12:0/14:1(9Z) and PC13:0/13:0 were expected to have no effect and have been found to have no affect. Not available indicates no commercial purified product available.

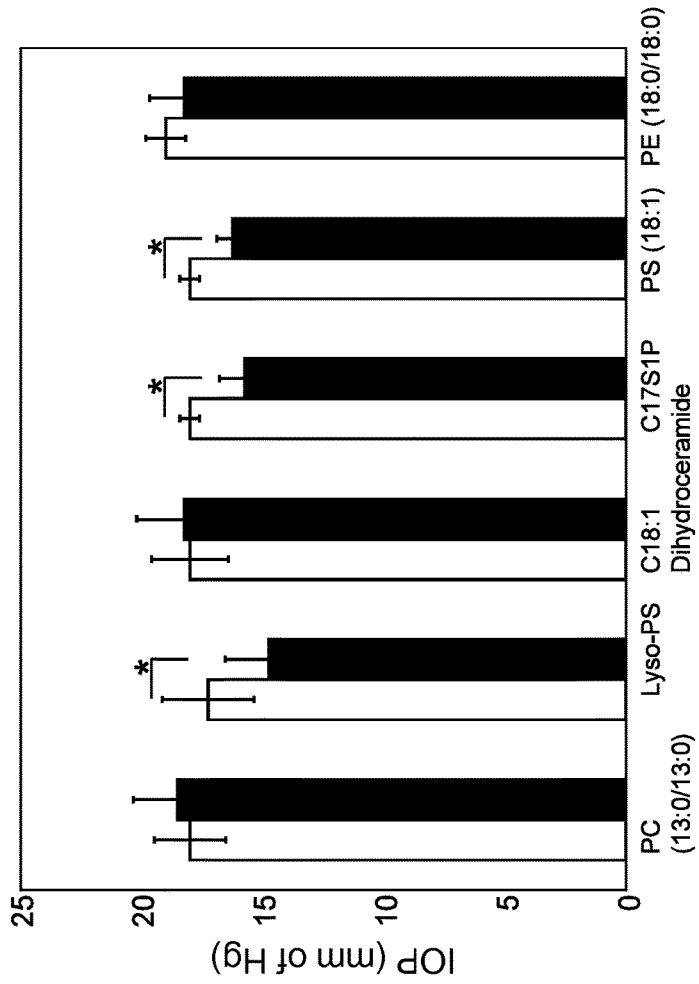

Figure 13

The IOP lowering in normotensive cynomolgus monkeys. Lipids were topically applied in 1 µl volume around ~1 pm in the afternoon. The right eye was treated with vehicle (5% DMSO) alone, and the left eye was treated with 10 picoM (in 5% DMSO) PC(13:0/13:0), Lyso-PS, C18:1 Dihydroceramide, PS(18:1), or PE (18:0/18:0) or 50 nM C17S1P for 5 days. Monkeys were subjected to slit lamp examination and IOP measurement prior to and after treatment. The IOP measurement obtained at 3-6 hours post-treatment with lipid on the fifth day of treatment is depicted as solid bars. The hollow bars are control.

COMPOSITIONS AND METHODS FOR REDUCING INTRAOCULAR PRESSURE

CROSS-REFERENCE TO RELATED APPLICATION

This application claims priority to U.S. Provisional Patent Application No. 61/912,070, filed Dec. 5, 2013, which is incorporated by reference herein in its entirety.

STATEMENT REGARDING FEDERALLY SPONSORED RESEARCH OR DEVELOPMENT

This invention was made with government support under grant numbers NIH EY016112S1 and NIH R01 EY016112 awarded by the National Institutes of Health. The government has certain rights in the invention.

FIELD OF THE INVENTION

The invention relates generally to the fields of ophthalmology and biochemistry. More particularly, the invention relates to compositions including lipids for reducing intraocular pressure and methods of use thereof.

BACKGROUND

Glaucoma refers to a group of blinding neuropathies including primary open angle glaucoma (POAG), in which aqueous outflow is impeded resulting in increased intraocular pressure (IOP), and normal tension glaucoma (NTG), where pressure remains within a normal range but progressive loss of vision occurs. Worldwide, glaucoma affects over 60.5 million individuals, rendering it an enormous health problem. Elevated IOP is thought to damage the optic nerve resulting in progressive and irreversible blindness in glaucoma. Reduction in IOP remains the only proven therapy against glaucoma. Reduced aqueous humor (AH) outflow due to increased resistance to the former at the trabecular meshwork (TM), a tiny filter like region in the anterior eye, is attributed to elevated IOP. Prostaglandins (PGs), identified in the iris in 1955 as a smooth muscle stimulating substance, remain the only lipid class that is effective therapy for glaucoma as a topical application since 1997. The normal path of aqueous outflow is through the TM and is termed the conventional pathway. In the event of spikes of abnormal elevated pressure, an auxiliary pathway termed the uveoscleral pathway is often tapped transiently. Prostaglandin analogs increase aqueous outflow via the uveoscleral pathway. Except for pilocarpine, whose efficacy as a glaucoma drug is inferior to prostaglandins and with significant side effects, no known drug exists that increases the conventional outflow pathway. Thus, development of new therapeutics targeting the conventional pathway is warranted.

SUMMARY

Disclosed herein are compositions, kits, and methods for reducing IOP in a subject (e.g., human). The compositions include at least one naturally occurring or synthesized version thereof or analog thereof of a lipid (e.g., a phosphatidylserine, a phosphatidylcholine, a phosphatidylethanolamine, a sphingomyelin, a sphingoid base or a sphingoid base-1-phosphate, a psychosine or other glycolipid) that is endogenous to non-glaucomatous AH but absent from or present in low levels (typically, for example, 15 femtomoles or less per µg of AH proteins) glaucomatous AH in a subject and that lowers IOP in a glaucomatous subject, in a therapeutically effective amount for promoting aqueous outflow through TM in at least one eye of the glaucomatous subject and reducing IOP in the glaucomatous subject. The compositions can be used for treating glaucomas, including, for example, POAG and NTG. Described herein is the discovery of new lipids (e.g., phosphatidylserines, phosphatidylcholines, phosphatidylethanolamines, sphingomyelin, sphingoid base or sphingoid base-1-phosphate, psychosine and other glycolipids) that are endogenous to non-glaucomatous AH but absent from or present at low (decreased) levels in glaucomatous AH and that enable IOP regulation in mammals.

The identification of endogenous lipids in the AH and identification of lipid changes associated with glaucoma as described herein provides new insight into the homeostatic control of IOP and the role of trabecular meshwork cells towards the same. Identification and quantification of endogenous lipids in the AH was previously a challenge due to the necessity of an unusually large and diverse chemistry for identification of diverse molecules and the need for a high amount (≥0.5 µg of individual species) of purified lipid species by the usual chromatographic and/or nuclear magnetic resonance (NMR) techniques. The discoveries described herein remove both of these barriers. Class-specific analyses of lipids of the AH and TM in both humans (between control non-glaucoma and POAG) and in DBA/2J mice (between normotensive, hypertensive and post-elevation state) using moderate resolution mass spectrometry revealed important differences between control and glaucoma. DBA/2J is a mouse model of glaucoma that develops spontaneous elevation in IOP around 8 months, thus less than 8 months of age can be considered as normotensive, 8-12 months as hypertensive state in DBA/2J mice. Beyond 12 months, the IOP undergoes a natural lowering believed to be due to decreased production of AH. DBA/2J mice often show pigmentary dispersion, however, spontaneous IOP elevation and degree of IOP elevation do not correlate with the extent of pigmentary dispersion. In humans the pigment dispersion often clears up without inducing IOP elevation and that injection of dispersed pigment materials into cadaver eyes does not result in significant IOP elevation. A large cohort of DBA/2J mice lacks correlation between pigment dispersion and IOP elevation. In a genetically identical line of DBA/2J termed DBA/2-Gpnmb+-Sj/J mice, over-expression of the 66 kDa protein cochlin results in IOP elevation but not ~66 kDa serum albumin or RPE65 protein, suggesting that the elevation of IOP is far more complex than simple clogging of the TM by a protein or by pigment dispersion. Described herein are results of biological assays of identified endogenous lipids in the AH (Table 1 (FIG. 11)) that have demonstrated lowering of IOP after topical application in four different mouse models. The following biological assays were used for characterization of these endogenous lipids: (1) role in primary trabecular meshwork cell mobility and shape, (2) the expansion and/or contraction of gel matrix with embedded primary TM cells, (3) transport of fluorescin across an assembled layer of primary cell over a permeable filter paper in a Using type chamber, and (4) assessment of their ability to reduce IOP and stemming vision loss in four different murine model of glaucoma ((a) DBA/2J, (b) cochlin-overexpression, (c) CTGF-overexpression and finally (d) in transgenic mycilin mutant mice [Tg-MYOC(Y437H)]).

Accordingly, described herein is a composition for reducing intraocular pressure (IOP) in a subject. The composition includes a pharmaceutically acceptable vehicle and at least one naturally occurring or synthesized version thereof or analog thereof of a lipid that is endogenous to non-glaucomatous aqueous humor in a subject. In various embodiments, the lipid is a phosphatidylserine, a phosphatidylcholine, a phosphatidylethanolamine, a sphingomyelin, a sphingoid base, a sphingoid base-1-phosphate, a ceramide, a cholesterol, a psychosine or other glycolipid, which lowers IOP in a subject. The lipid is provided in a therapeutically effective amount for promoting aqueous outflow through TM in at least one eye of the subject and reducing IOP in the subject.

Also described herein is a composition for reducing intraocular pressure in a subject. The composition includes a pharmaceutically acceptable vehicle and at least one of the following lipids: PC(12:0/14:1(9Z)), PE(18:0/18:0), PS(14:0/0:0), PS(18:0/0:0), PS18:0 Lyso-PS, PS: 18:1, PI(12:0/17:2)9Z,12Z)), PI(18:0/20:4(5Z,8Z,11Z,14Z)), Cer(d18:0/18:1(9Z)), C18:1 Dihydroceramide (d18:0/18:1(9Z)) (N-oleoyl-D-erythro-sphinganine), Cer(d18:1/26:1(17Z)), SM(d16:1/25:0), Sphinganine, and C17 Sphinganine-1-phosphate, in a therapeutically effective amount for promoting aqueous outflow through TM in at least one eye of the subject and reducing intraocular pressure in the subject. The composition is typically formulated for topical administration. In one embodiment, the composition includes two or more of the following lipids: PC(12:0/14:1(9Z)), PE(18:0/18:0), PS(14:0/0:0), PS(18:0/0:0), PS18:0 Lyso-PS, PS: 18:1, PI(12:0/17:2)9Z,12Z)), PI(18:0/20:4(5Z,8Z,11Z,14Z)), Cer(d18:0/18:1(9Z)), C18:1 Dihydroceramide (d18:0/18:1(9Z)) (N-oleoyl-D-erythro-sphinganine), Cer(d18:1/26:1(17Z)), SM(d16:1/25:0), Sphinganine, and C17 Sphinganine-1-phosphate. The composition can further include a prostaglandin and/or prostaglandin analog. The pharmaceutically acceptable vehicle can be, for example, dimethylsulphoxide (DMSO), polyethylene glycol 400 or d-α-tocopherol propylene glycol 1000 succinate.

Further described herein is a composition for reducing intraocular pressure in a subject. The composition includes a pharmaceutically acceptable vehicle and an analog of at least one of the following lipids: PC(12:0/14:1(9Z)), PE(18:0/18:0), PS(14:0/0:0), PS(18:0/0:0), PS18:0 Lyso-PS, PI(12:0/17:2)9Z,12Z)), PI(18:0/20:4(5Z,8Z,11Z,14Z)), Cer(d18:0/18:1(9Z)), C18:1 Dihydroceramide (d18:0/18:1(9Z)) (N-oleoyl-D-erythro-sphinganine), Cer(d18:1/26:1(17Z)), SM(d16:1/25:0), Sphinganine, and C17 Sphinganine-1-phosphate, in a therapeutically effective amount for promoting aqueous outflow through TM in at least one eye of the subject and reducing intraocular pressure in the subject. The composition is typically formulated for topical administration. The composition can include two or more analogs of two or more of the following lipids: PC(12:0/14:1(9Z)), PE(18:0/18:0), PS(14:0/0:0), PS(18:0/0:0), PS18:0 Lyso-PS, PI(12:0/17:2)9Z,12Z)), PI(18:0/20:4(5Z,8Z,11Z,14Z)), Cer(d18:0/18:1(9Z)), C18:1 Dihydroceramide (d18:0/18:1(9Z)) (N-oleoyl-D-erythro-sphinganine), Cer(d18:1/26:1(17Z)), SM(d16:1/25:0), Sphinganine, and C17 Sphinganine-1-phosphate. The composition can further include a prostaglandin and/or prostaglandin analog. The pharmaceutically acceptable vehicle can be, for example, dimethylsulphoxide (DMSO), polyethylene glycol 400 or d-α-tocopherol propylene glycol 1000 succinate.

Still further described herein is a method of reducing intraocular pressure in a subject. The method includes administering to the subject a composition including a pharmaceutically acceptable vehicle and a phosphatidylserine, a phosphatidylcholine, a phosphatidylethanolamine, a sphingomyelin, a sphingoid base, a sphingoid base-1-phosphate, a ceramide, a cholesterol, a psychosine or other glycolipid, which lowers IOP in a subject and which is present in non-glaucomatous AH but which is absent in glaucomatous AH or only present at very low levels in glaucomatous AH (e.g., at least 1000-fold less in glaucomatous AH compared to non-glaucomatous AH, or 15 femtomoles or less per μg of AH proteins). Examples of lipid species that reduce intraocular pressure and are suitable in various aspects of the composition and method described herein are provided in Example 2. In various embodiments, the method comprises administering to the subject a composition comprising a pharmaceutically acceptable vehicle and at least one of the following lipids: PC(12:0/14:1(9Z)), PE(18:0/18:0), PS(14:0/0:0), PS(18:0/0:0), PS18:0 Lyso-PS, PS: 18:1, PI(12:0/17:2)9Z,12Z)), PI(18:0/20:4)5Z,8Z,11Z, 14Z)), Cer(d18:0/18:1(9Z)), C18:1 Dihydroceramide (d18:0/18:1(9Z)) (N-oleoyl-D-erythro-sphinganine), Cer(d18:1/26:1(17Z)), SM(d16:1/25:0), Sphinganine, and C17 Sphinganine-1-phosphate, or an analog thereof, in a therapeutically effective amount for promoting aqueous outflow through TM in at least one eye of the subject and reducing intraocular pressure in the subject. In a typical embodiment, the subject has glaucoma (e.g., primary open angle glaucoma or normal tension glaucoma) and administration of the composition reduces or prevents vision loss in the subject. In this regard, a method of treating or preventing glaucoma is also provided wherein a composition described herein is administered to subject in an amount effective to treat or prevent glaucoma.

In one embodiment, the composition is formulated for topical administration and is administered to the patient topically at least once per day. In any embodiment of the method described herein, the composition can include two or more of the following lipids: PC(12:0/14:1(9Z)), PE(18:0/18:0), PS(14:0/0:0), PS(18:0/0:0), PS18:0 Lyso-PS, PS: 18:1, PI(12:0/17:2)9Z,12Z)), PI(18:0/20:4)5Z,8Z,11Z, 14Z)), Cer(d18:0/18:1(9Z)), C18:1 Dihydroceramide (d18:0/18:1(9Z)) (N-oleoyl-D-erythro-sphinganine), Cer(d18:1/26:1(17Z)), SM(d16:1/25:0), Sphinganine, and C17 Sphinganine-1-phosphate. Similarly, the composition can include two or more analogs of two or more of the following lipids: PC(12:0/14:1(9Z)), PE(18:0/18:0), PS(14:0/0:0), PS(18:0/0:0), PS18:0 Lyso-PS, PS: 18:1, PI(12:0/17:2)9Z,12Z)), PI(18:0/20:4)5Z,8Z,11Z,14Z)), Cer(d18:0/18:1(9Z)), C18:1 Dihydroceramide (d18:0/18:1(9Z)) (N-oleoyl-D-erythro-sphinganine), Cer(d18:1/26:1(17Z)), SM(d16:1/25:0), Sphinganine, and C17 Sphinganine-1-phosphate. In the method, the composition can further include a prostaglandin and/or prostaglandin analog. The method can further include administering a second composition including a prostaglandin and/or prostaglandin analog to the subject. In such an embodiment, the composition including the at least one lipid or analog thereof and the second composition are administered to the subject concomitantly or at different times (e.g., at first and second time points).

Yet further described herein is a kit for reducing intraocular pressure in a subject. A typical kit includes: i) a composition including a pharmaceutically acceptable vehicle and at least one of the following lipids: PC(12:0/14:1(9Z)), PE(18:0/18:0), PS(14:0/0:0), PS(18:0/0:0), PS18:0 Lyso-PS, PS: 18:1, PI(12:0/17:2)9Z,12Z)), PI(18:0/20:4)5Z,8Z,11Z, 14Z)), Cer(d18:0/18:1(9Z)), C18:1 Dihydroceramide (d18:0/18:1(9Z)) (N-oleoyl-D-erythro-sphinganine), Cer(d18:1/26:1(17Z)), SM(d16:1/25:0), Sphinganine, and C17 Sphinganine-1-phosphate, or an analog thereof, in a therapeutically effective amount for promoting aqueous outflow through TM in at least one eye of the subject and reducing intraocular pressure in the subject; ii) instructions for use; and iii) packaging. The composition is preferably sterile and ready for administration.

Unless otherwise defined, all technical terms used herein have the same meaning as commonly understood by one of ordinary skill in the art to which this invention belongs.

By the term "lipid" is meant fatty acids and their derivatives, and substances related biosynthetically or functionally to these compounds. The term encompasses naturally occurring as well as synthetic lipids. The term also encompasses analogs of naturally occurring and synthetic lipids.

By the terms "analog" and "derivative" is meant any molecule modified, relative to a parent molecule, that retains at least some partial structure and biological function (or improved biological function) of the parent molecule. A biological function, for example, is the ability to lower IOP.

As used herein, "protein" and "polypeptide" are used synonymously to mean any peptide-linked chain of amino acids, regardless of length or post-translational modification, e.g., glycosylation or phosphorylation.

As used herein, the term "treatment" is defined as the application or administration of a therapeutic agent to a subject or patient, or application or administration of the therapeutic agent to an isolated tissue or cell from a subject or patient, who has a disease, a symptom of disease or a predisposition toward a disease, with the purpose to cure, heal, alleviate, relieve, alter, remedy, ameliorate, improve or affect the disease, the symptoms of disease, or the predisposition toward disease.

As used herein, the phrase "safe and effective amount" refers to the quantity of a component which is sufficient to yield a desired therapeutic response without undue adverse side effects (such as toxicity, irritation, or allergic response) commensurate with a reasonable benefit/risk ratio when used in the manner of this invention. By "therapeutically effective amount" is meant an amount of a composition of the present invention effective to yield the desired therapeutic response, for example, an amount effective to increase aqueous outflow through the TM and reduce IOP in an individual. The specific safe and effective amount or therapeutically effective amount will vary with such factors as the particular condition being treated, the physical condition of the patient, the type of mammal or animal being treated, the duration of the treatment, the nature of concurrent therapy (if any), and the specific formulations employed.

The terms "patient" "subject" and "individual" are used interchangeably herein, and mean a vertebrate subject, typically a mammalian subject (e.g., human, rodent, non-human primates, canine, bovine, ovine, equine, feline, etc.) who is to be treated, who has been treated, or who is being considered for treatment, and/or to obtain a biological sample from, with human patients being preferred. In some cases, the methods, kits, and compositions described herein find use in experimental animals, in veterinary applications, and in the development of animal models for disease, including, but not limited to, rodents including mice, rats, and hamsters, as well as non-human primates.

Although compositions, kits, and methods similar or equivalent to those described herein can be used in the practice or testing of the present invention, suitable compositions, kits, and methods are described below. All publications, patent applications, and patents mentioned herein are incorporated by reference in their entirety. In the case of conflict, the present specification, including definitions, will control. The particular embodiments discussed below are illustrative only and not intended to be limiting.

BRIEF DESCRIPTION OF THE DRAWINGS

FIGS. 1A and 1B show representative mass spectrometric data demonstrating the disappearance of a PC species in glaucomatous AH compared to normal controls. Electrospray ionization mass spectrometric analysis of phosphatidylcholines (PC) class of lipids in human aqueous humor (AQH) in positive-ion mode. A. and B. are representative analysis of human glaucomatous and normal AH as indicated with an internal standard (arrowhead; m/z ratio of 650.6) was used for ratiometric quantification. Parent ion scan was performed for m/z 600-900. Arrow shows presence of a unique species in normal AH.

FIGS. 2A and 2B show representative images of the effect of lipid on trabecular meshwork primary cells. The time lapsed images of cell at indicated time interval. A. The control TM cells were subjected to vehicle (5% DMSO) in phosphate buffered saline. Most cells in the control group remain rounded or only somewhat elongated with a few that showed having a protrusion. A protrusion of filopodia in a cell is indicated by thick arrow head. At 2 minutes after addition of vehicle to 16 minutes, the protrusion remains unchanged. B. TM cells treated with 10 pmoles of lipid. Most cells have protrusions with only a few cells without them. The filopodia in lipid treated cells are dynamic, they undergo dynamic retraction starting at 1 or 2 minutes after addition of lipid in the serum free media, indicated by arrows. At 16 minutes filopodia are largely retracted.

FIG. 3 shows results from the collagen gel embedded expansion and/or contraction assay. About 10,000 primary TM cells were placed in a capillary tube with rat collagen without (control) or after treatment with 10 pmole of indicated lipid. The change in collagen column length was measured at the end of 24 hours. Mean and standard deviation from three independent experiments are presented. As shown by yellow/gray zones, the expansions were categorized into four zones (2, 3 and 4 are identified), 1=>1.0 mm; 2=1.0 to 1.4 mm; 3=>1.4 mm but <2.0 mm; 4=2.0 and >2.0 mm.

FIG. 4 shows results from the fluorescein transport assay across a multilayer of primary TM cells in an Using type chamber. A pentalayer of cells were casted on a PVDF filter of 0.45 µm pore size with second to fourth layer topped with rat collagen. Control (without lipid treatment) or with 10 pmole of indicated lipid treated cells were used for these measurements. The transport of flourescein at 15 seconds from the opposite end after introduction of sample at one was estimated. Mean and standard deviation from three independent experiments have been presented. The relative transport has been divided into two zones (marked in yellow), that when the transport is above 0.48 but less than 0.62=1; and above 0.62=2 as indicated.

FIG. 5 shows measurement of intraocular pressure in mice using topical application of 10 pmole of indicated lipid in 5% DMSO (vehicle) in 1 µl administered during 1-4 pm in the afternoon. The right eye was treated with vehicle alone and left eye treated with lipid. Control had both eyes treated with vehicle. A. In DBA/2J mice the indicated lipid in vehicle or control (vehicle only) were administered one daily at around 7.5 months of age in mice which were noted to have a IOP≥18 mm of Hg (20% increase from an average baseline of 15 mm of Hg was employed as treatment point). The average IOP recordings are shown for indicated lipids. B. A 10 picomole each of six PC (13:0/13:0; PE (18:0/18:0), Lyso-PS 18:0, PS 18:1, Sphinganine and C17S1P) were combined and applied as a topical dose once daily for up to 7 days on DBA/2J mouse eyes in 5% DMSO (vehicle). The other eye received only the vehicle and did not show lowering of IOP. The combination of these lipids showed much better lowering of the IOP compared to control or other individual drugs including commercially available drugs Xalatan, Timolol (FIG. 5B) or Dorzolamide (not shown, have the same level of IOP reduction as Timolol). Transgenic myocillin mice [Tg-MYOC(Y437H)] subjected to a topical dose of indicated lipids as noted above (FIG. 5C). The IOP lowering compared to control was noted on day 4 and 6 as shown.

FIGS. 6A-6C show a schematic illustration of an approach to identify protein targets of lipids. A. The 10 pmole of identified lipid in 5% DMSO (vehicle) was applied on to 40% confluent primary TM cells and after incubation of 1 minute subjected to UV cross linking in a UV Stratalinker 1800 cross-linker for about 1 minute. B. The cells were subjected to lysis with 1% SDS and protein extracts were fractionated over a 4-20% gradient SDS-PAGE. C. The same SDS-PAGE stained with Coommassie blue.

FIG. 7 shows select fluorescent analogs of a phosphatidylserine (PS) lipid, PS (18:1) used for cross-linking and mechanistic studies. Four analogs 18:1-0.6:0 NBD PS, 18:1 NBD PS, 18:1-12:0 NBD PS and 18:1 Dansyl PS are shown. The backbone is similar to PS (18:1) and the fluorescent part with their mass to charge ratio (m/z) is shown below each compound. The m/z of the compound below each of these parent entities refers to abundance of different isotopic variants due to incorporation of C-13 species in them.

FIGS. 9A-9C show lipid production in mixed culture of ciliary body. A. The organ culture of ciliary body (CB) after enucleation, excision and thorough washing, the CB was placed in serum free medium. B. The outside view of the same CB as in A. C. Detection of lipids at time interval in the serum free medium at indicated time point.

FIGS. 10A-10B are schematic diagrams of the anterior chamber of the eye depicting the (A) conventional and (B) uveoscleral pathways.

FIG. 11 is Table 1 which lists aqueous humor (AH) lipids that are unique in both control DBA2J and humans (i.e., non-glaucomatous DBA2J and humans) compared to glaucomatous AH.

FIG. 13 is a bar graph demonstrating the effect of six lipids (x-axis) on intraocular pressure (mm of Hg, y-axis) in normotensive cynomolgus monkeys. Lipids were topically administered in 1 µl volume around ~1 pm in the afternoon. The right eye was treated with vehicle alone, and the left eye was treated with lipid. The cynomolgus monkeys (n=4) were treated with 10 picoM lipid (except C17S1P which was 50 nM) for 5 days. Monkeys were subjected to slit lamp examination and IOP measurement prior to and after treatment. The IOP measured 3-6 hours post-treatment on the fifth day of treatment is depicted as solid bars. The hollow bars are control (vehicle only (5% DMSO)).

DETAILED DESCRIPTION

Figure 8A:
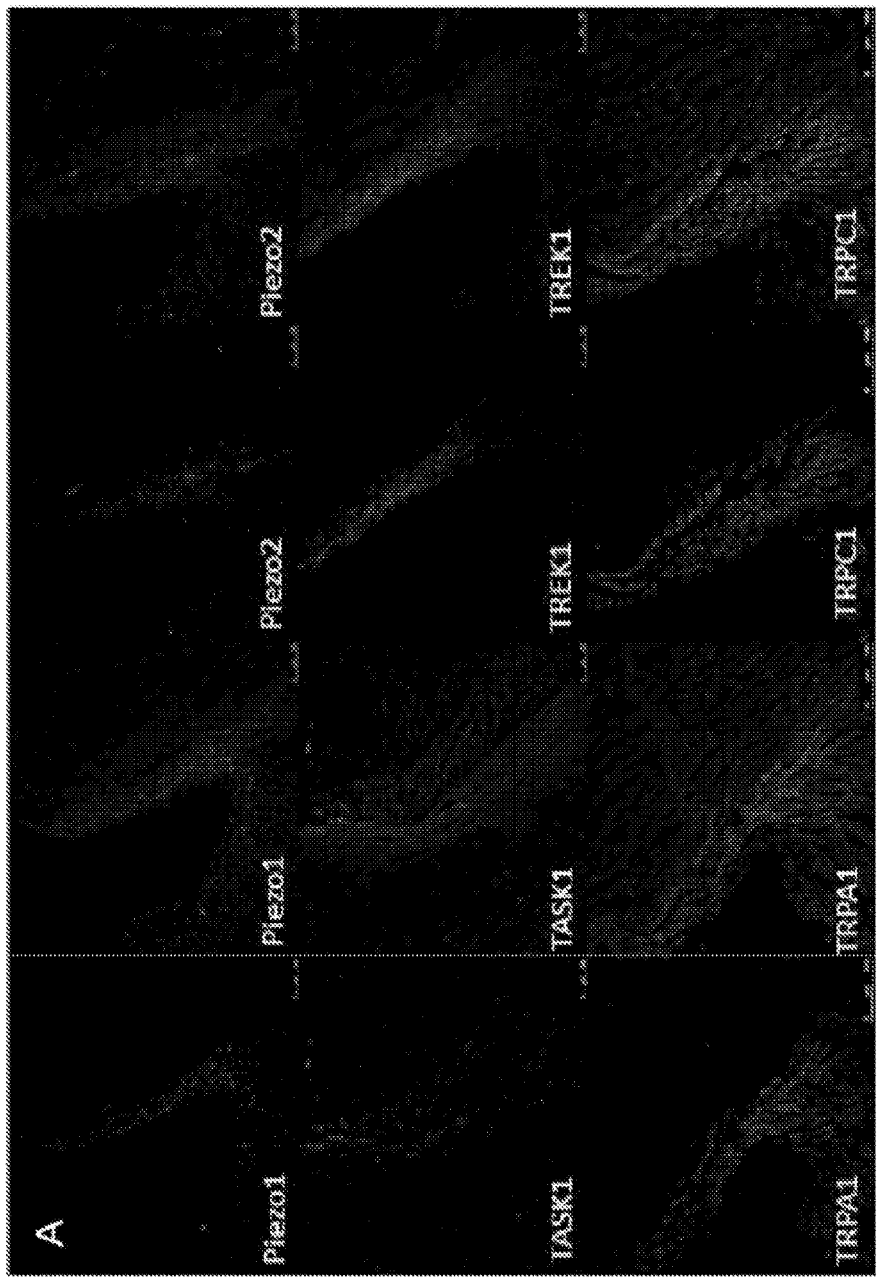
FIG. 8A is a series of micrographs showing identification of channels in the human TM tissue. About 11 of these channels were initially identified as cross-linked protein to one or more lipids within first 2 minutes of incubation of TM cells with PS (18:1) lipid analogs.
Figure 8B:
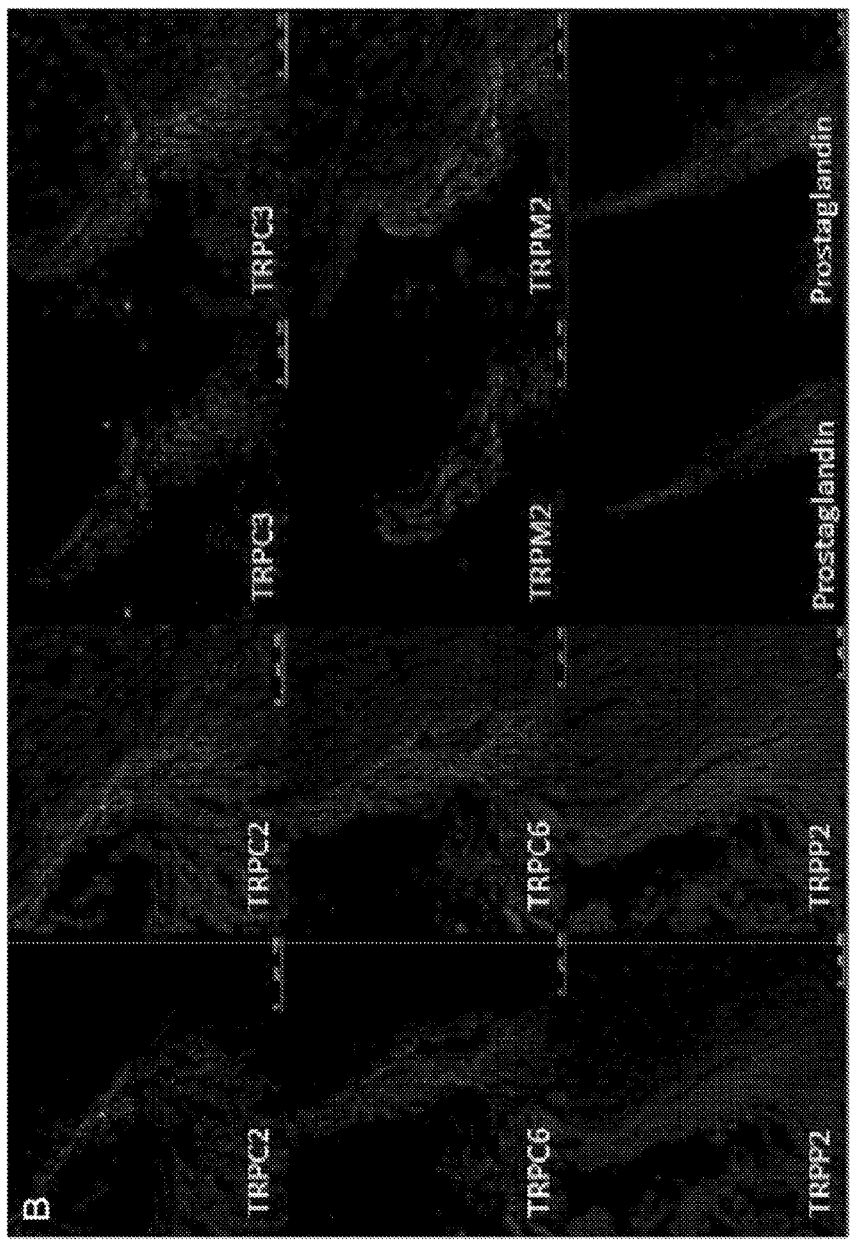
FIG. 8B is a series of micrographs showing identification of channels in the human TM tissue. About 11 of these channels were initially identified as cross-linked protein to one or more lipids within first 2 minutes of incubation of TM cells with PS (18:1) lipid analogs.
Figure 8C:
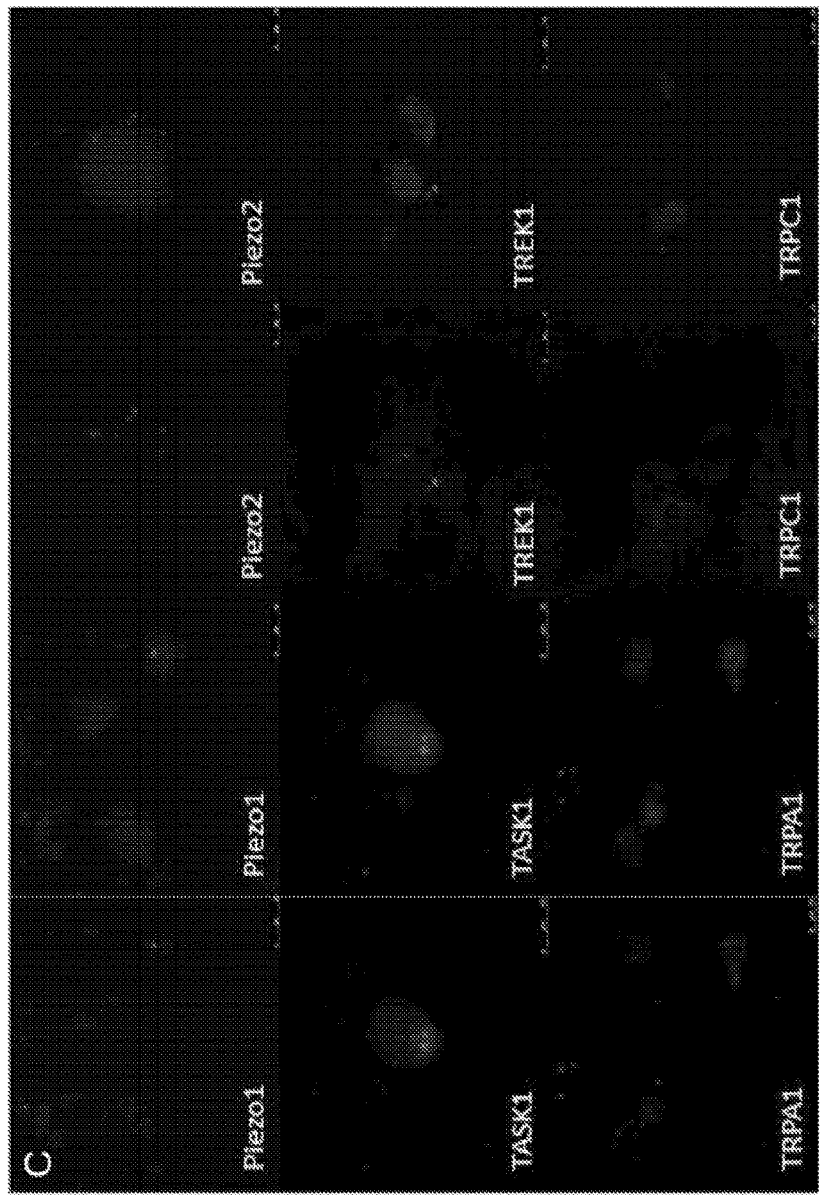
FIG. 8C is a series of micrographs showing identification of channels in the human TM derived primary cells. About 11 of these channels were initially identified as cross-linked protein to one or more lipids within first 2 minutes of incubation of TM cells with PS (18:1) lipid analogs.
Figure 8D:
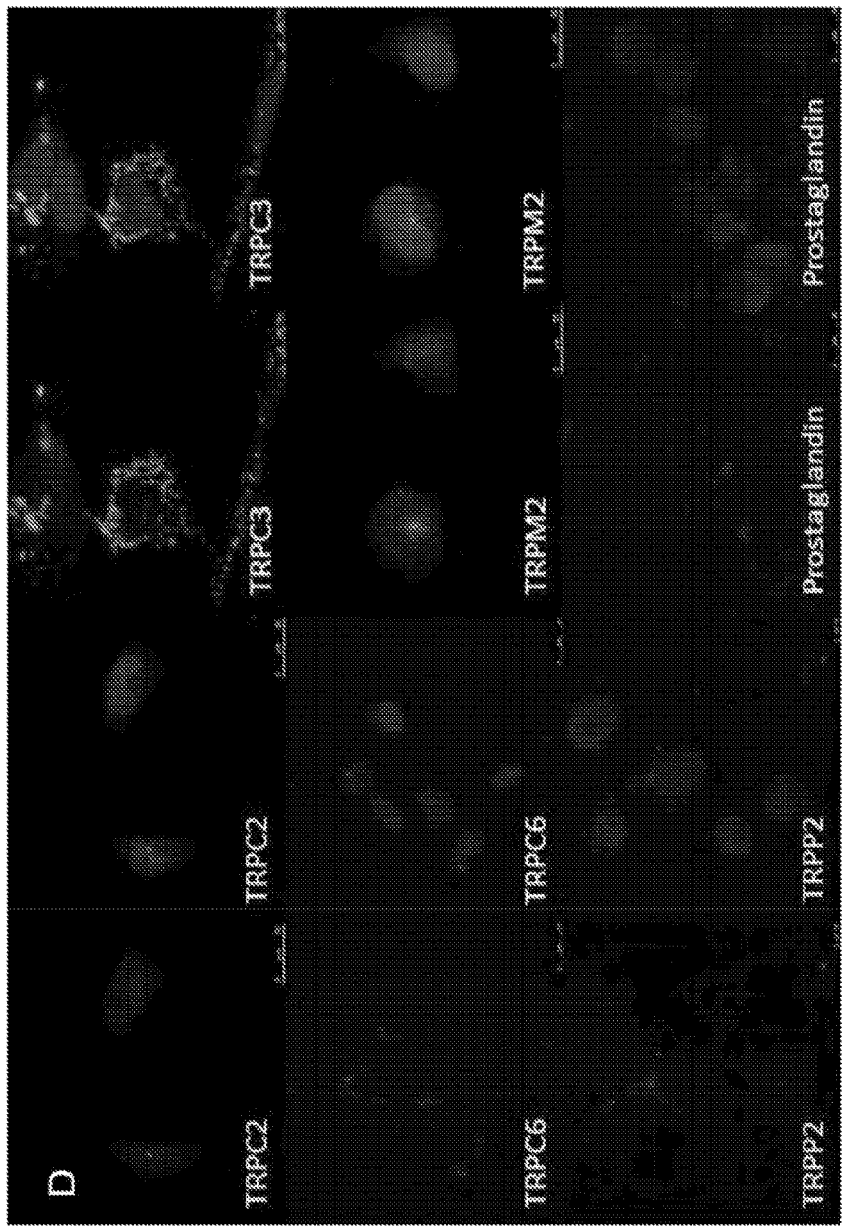
FIG. 8D is a series of micrographs showing identification of channels in the human TM derived primary cells. About 11 of these channels were initially identified as cross-linked protein to one or more lipids within first 2 minutes of incubation of TM cells with PS (18:1) lipid analogs.

Compositions and kits for reducing IOP in a subject (e.g., human) include at least one naturally occurring or synthesized version thereof or analog thereof of a lipid (e.g., a phosphatidylserine, a phosphatidylcholine, a phosphatidylethnolamine, a sphingomyeline, a sphingoid base, a sphingoid base-1-phosphate, a psychosine or other glycolipid) that is endogenous to non-glaucomatous AH but absent from or present at low levels in glaucomatous AH and that when administered (e.g., topical addition) to a glaucomatous subject, lowers IOP by promoting aqueous outflow through TM in at least one eye of the subject. Methods of reducing IOP in a subject and treating glaucoma in a subject include administering such compositions. The compositions, kits and methods can be used for treating any type of glaucoma, including, for example, POAG and NTG.

The below described preferred embodiments illustrate adaptations of these compositions, kits, and methods. Nonetheless, from the description of these embodiments, other aspects of the invention can be made and/or practiced based on the description provided below and are contemplated as part of the invention.

Biological Methods

Methods involving conventional molecular biology techniques are described herein. Such techniques are generally known in the art and are described in detail in methodology treatises such as Molecular Cloning: A Laboratory Manual, 3rd ed., vol. 1-3, ed. Sambrook et al., Cold Spring Harbor Laboratory Press, Cold Spring Harbor, N.Y., (2001); and Current Protocols in Molecular Biology, ed. Ausubel et al., Greene Publishing and Wiley-Interscience, New York, (1992) (with periodic updates). Biochemistry techniques are generally known in the art and are described in detail in methodology treatises such as A Manual for Biochemistry Protocols (Manuals in Biomedical Research) M. R. Wenk, A. Z. Fernandis, World Scientific Publishing Company; 1st edition (Mar. 30, 2007). Methods of synthesizing lipids are also well known in the art, and are described in treatises such as Lipid Synthesis and Manufacture, by Frank D Gunstone Ed., Almond Pr (1999).

Compositions for Reducing Intraocular Pressure in a Subject

Described herein are lipids and lipid-containing compositions which are administered to a subject (e.g., a human having glaucoma) in order to reduce intraocular pressure. In a typical embodiment, a composition for reducing intraocular pressure in a subject includes a pharmaceutically acceptable vehicle and at least one naturally occurring or synthesized version thereof or analog thereof of a lipid that is endogenous to non-glaucomatous AH but absent from or present at low (decreased) levels in glaucomatous AH in a subject, that is a phosphatidylserine, a phosphatidylcholine, a phosphatidylethanolamine, a sphingomyelin, a sphingoid base, a sphingoid base-1 phosphate, ceramide, cholesterol, a psychosine or other glycolipid, and that lowers IOP in the subject. The at least one naturally occurring or synthesized lipid or analog thereof is in a therapeutically effective amount for promoting aqueous outflow through TM in at least one eye of the subject and reducing IOP in the subject. Any suitable phosphatidylserine, phosphatidylcholine, phosphatidylethanolamine, sphingomyelin, sphingoid base, sphingoid base-1 phosphate, ceramide, cholesterol, psychosine or other glycolipid that lowers IOP in a subject can be used. Examples of such lipids include those listed in Table 1 (FIG. 11) (i.e., PC(12:0/14:1(9Z)), PE(18:0/18:0), PS(14: 0/0:0), PS(18:0/0:0), PS18:0 Lyso-PS, PS: 18:1, PI(12:0/17: 2)9Z,12Z)), PI(18:0/20:4)5Z,8Z,11Z,14Z)), Cer(d18:0/18:1 (9Z)), C18:1 Dihydroceramide (d18:0/18:1(9Z)) (N-oleoyl-D-erythro-sphinganine), Cer(d18:1/26:1(17Z)), SM(d16:1/ 25:0), Sphinganine, and C17 Sphinganine-1-phosphate). Synthesized versions of naturally occurring lipids and analogs derivatives thereof can be used in compositions as described herein for reducing IOP and treating glaucoma. Referring to Table 1 (FIG. 11), all lipids listed are naturally occurring lipids endogenous to non-glaucomatous AH except for PS (18:1) which is an analog of PS (18:0/0:0). Analogs are designed such that they do not exert appreciable toxicity and do not lose the biological function of IOP reduction. Referring to FIGS. 7 and 8, fluorescent analogs of PS (18:1) have been generated and tested.

A composition for reducing IOP can include one, two or more (e.g., 2, 3, 4, 5, 6, 7, etc.) naturally occurring or synthetic lipids, or analogs thereof, endogenous to non-glaucomatous AH. A composition can include, for example, one, two or more of the lipids listed in Table 1 (FIG. 11). As another example, a composition can include one, two or more analogs of one, two or more lipids listed in Table 1 (FIG. 11). A composition for reducing IOP can further include a prostaglandin and/or prostaglandin analog.

The naturally occurring lipids, synthesized lipids, and analogs thereof described herein can be prepared by any suitable methods. Naturally occurring lipids can be obtained by, for example, by chromatographic separation from a plant source (for example, a naturally occurring lipid can be separated from oil of the mustard seeds). Alternatively, lipids can be synthesized using known techniques, including standard organic chemical synthesis. Large scale plant oil or the organic phase extraction of lipids from the eyes of cattles (pig or cow) will enable the chromatographic separation of a specific lipid from the mixture extracted in organic phase extraction (for example, Using Bligh and Dyer method or Folch method using chloroform and methanol mixtures). For organic synthesis, a precursor molecule which is readily available can be modified following standard organic chemical synthesis procedures. Once the naturally occurring lipid, synthetic lipid or analog thereof is obtained or synthesized, it is typically formulated with a pharmaceutically acceptable vehicle for topical administration. Any suitable pharmaceutically acceptable vehicle can be used (e.g., dimethylsulphoxide (DMSO), polyethylene glycol 400 or d-α-tocopherol propylene glycol 1000 succinate).

Methods of Reducing Intraocular Pressure in a Subject

Methods of reducing intraocular pressure in a subject are described herein. In one embodiment, the method includes administering to the subject a composition including a pharmaceutically acceptable vehicle and at least one naturally occurring or synthesized version thereof or analog thereof of a lipid that is endogenous to non-glaucomatous AH but absent from glaucomatous AH in a subject. The lipid, in various embodiments, is a phosphatidylserine, a phosphatidylcholine, a phosphatidylethanolamine, a sphingomyelin, a sphingoid base, a sphingoid base-1-phosphate, a ceramide, a cholesterol, a psychosine or other glycolipid, that lowers IOP in the subject. If the subject has glaucoma (e.g., primary open angle glaucoma or normal tension glaucoma), the composition is a therapeutically effective amount for treating the glaucoma and preventing or mitigating vision loss in the subject. In one embodiment of the method, the composition is formulated for topical administration and is administered to the subject (e.g., human patient having glaucoma) topically at least once per day. For example, 10-20 pmoles of a mixture of lipids will be added with 5% DMSO and a drop (or multiple drops) will be applied topically using a dropper to the eye. In the method, the composition can also include a prostaglandin or prostaglandin analog. In another embodiment, a first composition including at least one naturally occurring or synthesized version thereof or analog thereof of a lipid that is endogenous to non-glaucomatous AH but absent from glaucomatous AH in a subject, that is phosphatidylserine, a phosphatidylcholine, a phosphatidylethanolamine, a sphingomyelin, a sphingoid base, a sphingoid base-1-phosphate, a ceramide, a cholesterol, a psychosine or other glycolipid, and that lowers IOP in the subject is administered to the subject, and a second composition including a prostaglandin or prostaglandin analog is administered to the subject. In this embodiment, the first and second compositions can be administered to the subject concomitantly or at different (e.g., first and second) time points.

Kits for Reducing Intraocular Pressure in a Subject

Described herein are kits for reducing intraocular pressure and treating glaucoma in a subject. In one embodiment, a kit for reducing intraocular pressure in a subject includes a composition including a pharmaceutically acceptable vehicle and at least one naturally occurring or synthesized version thereof or analog thereof of a lipid that is endogenous to non-glaucomatous AH but absent from glaucomatous AH in a subject, that is phosphatidylserine, a phosphatidylcholine, a phosphatidylethanolamine, a sphingomyelin, a sphingoid base, a sphingoid base-1-phosphate, a ceramide, a cholesterol, a psychosine or other glycolipid, and that lowers IOP, and instructions for use. The kit can further include a second such lipid, and optionally, a prostaglandin or prostaglandin analog. In a kit, the instructions generally include one or more of: a description of the composition; dosage schedule and administration for treatment of glaucoma; precautions; warnings; indications; counter-indications; overdosage information; adverse reactions; animal pharmacology; clinical studies; and/or references. The instructions may be printed directly on the container (when present), or as a label applied to the container, or as a separate sheet, pamphlet, card, or folder supplied in or with the container. Generally, a kit as described herein also includes packaging. In some embodiments, the kit includes a sterile container which contains a therapeutic or prophylactic composition; such containers can be boxes, ampules, bottles, vials, tubes, bags, pouches, blister-packs, or other suitable container forms known in the art. Such containers can be made of plastic, glass, laminated paper, metal foil, or other materials suitable for holding cells or medicaments.

Effective Doses

The compositions described above are preferably administered to a mammal (e.g., non-human primate, bovine, canine, rodent, human) in an effective amount, that is, an amount capable of producing a desirable result in a treated subject (e.g., delaying, mitigating or preventing vision loss in the subject). Toxicity and therapeutic efficacy of the compositions utilized in methods described herein can be determined by standard pharmaceutical procedures. As is well known in the medical and veterinary arts, dosage for any one animal depends on many factors, including the subject's size, body surface area, age, the particular composition to be administered, time and route of administration, general health, and other drugs being administered concurrently.

The amount of the therapeutic agent (e.g., lipid) to be administered varies depending upon the manner of administration, the age and body weight of the patient, and with the pathology of the disease. A composition as described herein is typically administered at a dose of 10 picomole to 10 micromole.

Therapeutic compositions described herein can be administered to a subject by any suitable route. The composition may be provided in a dosage form that is suitable for local, topical, oral or systemic administration. If being applied topically, the composition is typically topically applied on the cornea from where it will easily percolate to the trabecular meshwork. The compositions typically include non-toxic pharmaceutically acceptable carriers and may be formulated according to conventional pharmaceutical practice (see, e.g., Remington: The Science and Practice of Pharmacy (20th ed.), ed. A. R. Gennaro, Lippincott Williams & Wilkins, (2000) and Encyclopedia of Pharmaceutical Technology, eds. J. Swarbrick and J. C. Boylan, Marcel Dekker, New York (1988-1999)).

EXAMPLES

The present invention is further illustrated by the following specific examples. The examples are provided for illustration only and should not be construed as limiting the scope of the invention in any way.

Example 1

Endogenous Lipid Regulators of Intraocular Pressure

Described herein is the first use of mass spectrometric methods for profiling lipid and subsequent biological assays with the identified lipids. Endogenous lipids [14 specific lipids, namely: PC(12:0/14:1(9Z)); PE(18:0/18:0); PS(14:0/0:0); PS(18:0/0:0); PS18:0 Lyso-PS; 18:1 PS; PI(12:0/17:2)9Z,12Z)); PI(18:0/20:4)5Z,8Z,11Z,14Z)); Cer(d18:0/18:1(9Z)); C18:1 Dihydroceramide (d18:0/18:1(9Z)) (N-oleoyl-D-erythro-sphinganine); Cer(d18:1/26:1(17Z)); SM(d16:1/25:0); Sphinganine and C17 Sphinganine-1-phosphate] were identified from screening the AH of human control and glaucoma patients to be present only in control AH but not in glaucomatous AH. In the following assays, (1) mobility and cell shape changes for trabecular meshwork (TM) primary cells due to exposure to lipids, (2) gel expansion assays/contraction assays that involve ensemble of cells in artificial embedment, and (3) assays to demonstrate transport of fluorescien in assembled layers of primary TM cells, showed an effect for all the listed lipids above except PC(12:0/14:1(9Z)). A non-mammalian lipid 1,2-ditridecanoyl-sn-glycero-3-phosphocholine PC(13:0/13:0) also showed lack of any effect in these assays. In a screening with DBA/2J mice that develop elevated IOP spontaneously around 8 months of age, lowering of IOP by PE(18:0/18:0); PS(14:0/0:0); PS(18:0/0:0); PS18:0 Lyso-PS; 18:1 PS; PI(12:0/17:2)9Z,12Z)); PI(18:0/20:4)5Z,8Z,11Z,14Z)); Cer (d18:0/18:1(9Z)); C18:1 Dihydroceramide (d18:0/18:1(9Z)) (N-oleoyl-D-erythro-sphinganine); Cer(d18:1/26:1(17Z)); SM(d16:1/25:0); Sphinganine and C17 Sphinganine-1-phosphate but not by PC(12:0/14:1(9Z)) and PC(13:0/13:0) was shown. Similar results were also found with cochlin-overexpression, CTGF-overexpression, and in transgenic mycilin mutant mice [Tg-MYOC(Y437H)].

Results

Elimination or substantial reduction of lipids in the glaucomatous aqueous humor. Extensive analyses of aqueous humor from moderate resolution mass spectrometer (TSQ Quantum Access Max) have shown a number of unique species in control AH that undergo a significant decrease in glaucoma (FIG. 1). With extensive analyses, levels of 14 entities (PC(12:0/14:1(9Z)), PE(18:0/18:0), PS(14:0/0:0), PS(18:0/0:0), PS18:0 Lyso-PS, 18:1 PS, PI(12:0/17:2)9Z, 12Z)), PI(18:0/20:4)5Z,8Z,11Z,14Z)), Cer(d18:0/18:1(9Z)), C18:1 Dihydroceramide (d18:0/18:1(9Z)) (N-oleoyl-D-erythro-sphinganine), Cer(d18:1/26:1(17Z)), SM(d16:1/25:0), Sphinganine, and C17 Sphinganine-1-phosphate) were found to be significantly lowered below the detection limit of the instrument (Table 1).

Modulation of cell motility and shape. Compared to controls (vehicle-10% DMSO only treated) shape of primary TM cells (FIG. 2A), exposure to lipids changed the shape of cells promoting filopodia and motility (FIG. 2B). All these lipids promote contraction of filopodia (FIG. 2B, arrows) and well as expansion. These images were derived from time lapsed video imaging of primary TM cells and summary data from several donor derived cells. The exposure to lipids render the cells more dynamic with respect to filopodia formation and their dynamic expansion-contraction (Summarized in Table 1 (FIG. 11)). The motility and filopodia formation is affected by a variety of intrinsic and extrinsic factors such as age of the donors from where cell have been derived, cell density, composition of the medium, environmental temperature and incubation gas composition. The age of the donor and cell density are the most prominent factors. Exposure to all lipids as noted in Table 1 (FIG. 11) [with the exception of PC(12:0/14:1(9Z)) and 1,2-ditridecanoyl-sn-glycero-3-phosphocholine PC(13:0/13:0)] resulted in a significant increase in dynamics of filopodia formation. This is most prominent in old donor derived TM cells where the dynamics of filopodia formation is significantly reduced but it is also discernible in younger donor-derived TM cells.

Properties of cell ensembles in embedded matrix and assembled layer of cells on filter membranes. Gel embedded primary TM cells in collagen matrix in capillary tubes were prepared following established protocols (Ilagan, R. et al. Biotechniques. 2010; 48: 153-5), and their ability within the first 24 hours for expansion or contraction of gels (control) or the cells which were subjected to treatment with lipids for 1 hour in serum free medium prior to gel embedding were determined. Lipids that modulate cell expansion in matrix embedded assay systems (FIG. 3) were found. The ability of the lipids to affect the gel embedded cell expansion are summarized in Table 1 (FIG. 11). These experiments using a slightly different setting, such as the incubation for a longer period of time, can demonstrate gel contraction instead of expansion. In these assays, all conditions were selected that resulted in gel expansion and not contraction (conditions that may show gel contraction were not used). The extent of expansion was divided into four zones 1, 2, 3, and 4 (FIG. 3). The higher the number, the greater is the expansion.

The transport of fluorescein across cell assembled layered TM cells was determined in an Using type chamber (FIG. 4). The five layers of primary TM cells with collagen matrix in between layers after the first layer were laid on a sterile PVDF membrane (0.45 μm pores). The fluorescein was introduced from one side of the port (the cellular side) and was sampled from another side (the membrane side) within 15 seconds of introduction. Differences in transport between the cell only control and cell treated with lipids for 1-3 hours prior to forming multi-layers (FIG. 4) was observed. The fluorescein transport was quantized and divided into two categories (marked with yellow zones) as 1 and 2 (FIG. 4). Table 1 (FIG. 11) presents a summary of the transport data using assembled layers of cells.

Taken together with cell mobility, gel expansion and fluorescein transport depicted as a number (range 1-4, the higher number is the greater intensity for measured property), a composite index was prepared (Table 1 (FIG. 11)). The lipids described herein may modulate TM cell behavior at the isolated cell level or at the cell ensemble level.

Intraocular pressure lowering in mouse models. The endogenous lipids lowered IOP in a DBA/2J mouse model of glaucoma (FIG. 5A). DBA/2J is the only known mouse animal where elevation of IOP occur spontaneously. Although this mouse also suffers from pigmentary dispersion, however, elevation of IOP appears not to correlate with IOP elevation. The lipids as indicated were applied as a topical dose (10 pmole in 5% DMSO as vehicle). The 5% DMSO only vehicle served as a control (FIG. 5A). Also determined was the lowering of IOP after elevation in IOP in DBA/2J after a short term application (FIG. 5B). A 10 picomole each of six PC (13:0/13:0; PE (18:0/18:0), Lyso-PS 18:0, PS 18:1, Sphinganine, and C17S1P) were combined and applied as a topical dose once daily for up to 7 days on DBA/2J mouse eyes in 5% DMSO (vehicle) (in other words, 10 picomoles of each PC was included). The other eye received only the vehicle and did not show lowering of IOP. As shown in FIG. 5B, the combination of these lipids showed much better lowering of the IOP compared to control or other individual drugs including commercially available drugs Timolol and Dorzolamide. Selected was a DBA/2J mouse at 8 months of age that showed an IOP of ~35 mm of Hg. Representative data is presented in FIG. 5B. Also used was a transgenic myocillin mutant mice [Tg MYOC(Y437H)] that shows elevated IOP in 3 months, for determination of IOP lowering by these lipids (FIG. 5C). In general these mice show an IOP of 24 mm of Hg and lipids showed lowering of IOP in this model as well (FIG. 5C). In addition to the DBA/2J model described here, these endogenous lipids lowered IOP in cochlin and connective tissue growth factor (CTGF) overexpression models. Over-expression was achieved in these mice using lentiviral vector mediated overexpression. Thus the endogenous lipids assessed here lowered IOP in vastly different DBA/2J and MYOC(Y437H) mouse models as well as in cochlin and CTGF overexpression models covering a broad swath of four rodent glaucoma models that encompass induced as well as spontaneous IOP elevation.

Protein targets of the lipids include mechanosensitive channels. As shown in FIG. 6, a strategy of UV cross-linking an analog of PS (18:1) and direct mass spectrometry of fluorescent bands were employed for identification of protein targets (FIG. 6). The various fluorescent analogs of PS (18:1) are shown in FIG. 7. Also used was PC 13:0/13:0 as a non-specific analog, thus protein bands showing cross linking with this non-specific analog were not subjected to mass spectrometry. Several mechanotransduction channels that get cross-linked with PS (18:1) (FIG. 8A, B, C) were identified. Earlier, independent of cross-linking, the existence of several of these channels in the TM and in primary TM cells was detected. A number of these channels were found to localize in the conventional outflow pathway (FIG. 8A) suggesting the possibility of an effect of endogenous lipids via the conventional pathway. The channels identified to cross-link with lipids were detected at mRNA (GEO database) and at protein levels to be present in the TM.

Endogenous lipids are generated in the ciliary body (CB). In glaucoma, CB and its aberration in the disease remains an under-investigated area. CB has not been targeted enough except for lowering production of AH. AH is thought to be produced in the CB. It was determined whether production of some of these lipids occurs in AH, which may suggest a homeostatic control of AH dynamics by the lipids and could be used for specific targeting in the future. It was found by mass spectrometry that in serum free culture, organ cultures of ciliary body (FIG. 9A, B) most of these lipids (Table 1 (FIG. 11); FIG. 9C) are generated. In other words, CB organ culture shows generation of these endogenous lipids, which showed biological activities and lowering of intraocular pressure in mouse models (FIG. 5). Thus, the ciliary body could be a potential specific target for treatment of glaucoma.

Summary of interpretation of the data. Endogenous lipids that are present in control human AH but not in glaucoma (Table 1 (FIG. 11)) were identified. All of these lipids also showed an absence in the trabecular meshwork of the hypertensive state of DBA/2J mice but not in the normotensive state. Exposure to these lipids showed changes in cellular properties and properties of assembled cell layers of gel embedded cells (FIG. 1-4). A correlation between an effect on these behaviors with lowering of elevated IOP (FIG. 5; Table 1 (FIG. 11)) was found. The IOP lowering showed three distinct kinetics: (a) by PS18:0 Lyso-PS and PS: 18:1; (b) by C18:1 Dihydroceramide (d18:0/18:1(9Z)) (N-oleoyl-D-erythro-sphinganine), sphinganine and C17 sphinganine-1-phosphate and (c) by PE(18:0/18:0). Based on differences in kinetics of IOP lowering, the mechanism of action is expected to be different for these three different types of lipid species. The aqueous outflow can occur via the conventional pathway (TM) and non-conventional or uveoscleral pathway (FIG. 10) (Goel, M., Picciani, R. G., Lee, R. K. & Bhattacharya, S. K. Open Ophthalmol J. 2010; 4: 52-59). Despite the evidence that in glaucoma the outflow is decreased by the conventional pathway, there is a lack of effective drugs that increase outflow via this pathway. The identification of mechanotransduction channels (FIG. 8A, B, C) and a predominant presence of several of them in the conventional pathway suggest these endogenous lipids may exert lowering of IOP utilizing this pathway. Finally, these lipids are generated by ciliary body. Thus their generation process may be future drug targets for improved glaucoma therapy.

Methods

TM cell culture experiments: Primary human TM cells were cultured from cadaveric corneo-scleral sections. The cells were isolated through a blunt dissection of the area containing and adjacent to the canal of Schlemm, followed by a 2 hour digestion in DPBS (cat #21-030-CV, Mediatech Inc, Manassas, Va.) suspension of 20% 0.01 µg/µL collagenase-A (cat #LS004194, Worthington, Lakewood N.J.). The blunt dissection and the proteolytic treatment were performed inside a 12 well culture plate (cat #665-180 Greiner Bio-One, Neuburg, Germany). Culture media containing [DMEM 1× (cat #10-017-CM, Mediatech Inc), 10% heat inactivated FBS (cat #35-016-CV, Mediatech), 0.5% 1.7 mM L-Glutamine (cat #G6392, Sigma-Aldrich), 1% Antibiotic-Antimycotic Solution (cat #30-004-CL, Mediatech)] was added after 2 hours to terminate digestion. A sterile microscopy slide (cat #56700-194, VMR) was placed on top of the tissue fragment to ensure bottom-contact and immobility inside the media well. The sections were cultured at 37° C. in 5% $CO_2$ inside a cell culture incubator. Culture was washed with 1× DPBS 7 days later to remove tissue debris; media change occurred every 3-4 days. Thus obtained cells were trypsin-treated (cat #25-050-C1, Mediatech) and accordingly distributed the day before the transfection complexes were created using the ratio of 0.4 µg/uL of respective vector DNA to the transfection agent (Lipofectamine 2000, cat #11668-019, Invitrogen), prepared accordingly to the manufacturer's instructions Following addition to respective wells, the transfection reactions were allowed to take place over a 2.5 hour span, after which they were terminated through the addition of cell culture media. Cell assays and immunohistochemical analysis were performed at or within a 24 hour time mark in order to observe and track the effects of vector expression on morphological changes. Time-lapse microscopy was performed using cells grown on glass bottom chamber slides (cat #154534, Lab-Tek, Thermo Fisher Scientific Inc., Rochester N.Y.) and Zeiss AxioVert 200M, for the duration of 20 hours, with a snapshot every 15 minutes, starting at 24 hours post-transfection. Immunohistochemical analysis was performed on cells fixed with 4% PFA (cat #19943, USB Corp, Cleveland, Ohio) at time intervals of 0, 24, and 29 hours post-transfection. Fixed cells were probed for cochlin, KCNK2 (TREK1), actin, annexin A2, α-TECT and DIAPH-1, using primary antibodies (cat #5370, Ayes Labs; cat #ab83932, Abcam; cat #R415, Invitrogen; cat #sc-1924, Santa Cruz Biotech.; cat #sc-18035, Santa Cruz Biotech., cat #HPA004916, Sigma-Aldrich) and imaged under confocal microscopy (Leica DM 6000 B) at magnification of 40×/63× with oil immersion. Media for excreted protein analysis was collected at 24 hours post transfection and subjected to ELISA probing for cochlin and annexin A2 (cat #sc-1924 Santa Cruz biotechnology, Inc.).

HEK-293T and COS-7 cells were transfected with plasmid expressing cochlin or annexin A2. 24 hours post-transfection, the media was collected and subjected to western blot analysis probing for cochlin and annexin A2. The cells were trypsin treated (Mediatech) and centrifuged at 1,000 RPM for 5 minutes. The supernatant was discarded and protein extraction buffer (as described for TM protein extraction) was added. The cells were centrifuged again at 10,000 RPM for 10 minutes. The supernatant obtained was then preserved and used for western blot analysis.

Using type chamber experiments: An Using type chamber (cat #USS1L, World Precision Instrument, Inc.) was used to measure fluorescein flow (sodium fluorescein dye) across the PVDF membrane (cat #75696E Pall Life Sciences, Pensacola Fla.). Trabecular meshwork cells were cultured as described above on the PVDF membrane. Before plating the cells a layer of collagen matrix (Rat Tail Collagen, cat #BD 354249) was formed on the membrane to facilitate the adherence of TM cells to the membrane. The cells were allowed to form a confluent monolayer over a period of 16-24 hours and then another layer of cells was plated on this monolayer. This process was repeated to ultimately achieve a confluent tri-layer of cells. The cells were transfected with DNA of interest [TREK-1+cochlin, TREK-1 and RPE65, TREK-1, transfection agent (Lipofectamine 2000) (Invitrogen)] or left untransfected. 24-36 hours post transfection the membranes were placed between the hemi-chambers of the apparatus connected to a peristaltic pump creating flow across the membrane bathing in 1× DPBS. To measure the flow across the membrane, sodium flourescein dye was used (1:100 dilution of 1 mg/ml). The dye was introduced in one hemi-chamber and equal amounts (100 µl) were aspirated from the other hemi-chamber at 5 minutes post-injection. The fluorescein intensity was measured using the spectrophotometer.

To demonstrate the formation of cochlin deposits in vitro, cochlin transfected TM cells were cultured on a PVDF membrane (Pall Life Sciences) with a pore size of 0.45 µM in a series of three confluent layers as described above. The membrane was then placed between the two hemi-vessels of the Using-type chamber connected to a standing column of serum-free cell culture media (DMEM 1×, Mediatech Inc) which was allowed to pass through the membrane by gravity, producing shear stress upon the cell layers as a result of the passage. Thus arranged setup was maintained for 12 hours, following which the membrane was embedded in O.C.T. and solidified using liquid nitrogen to permit sectioning. Obtained sections were subjected to immunohistochemical analysis probing for cochlin protein, using cochlin primary antibody (Ayes Labs) and imaging using the confocal setup (Leica DM6000 B).

Collagen gel expansion and/or contraction assay: Hydrogel solution was prepared using 10× MEM (cat #11430, Invitrogen), Sodium Bicarbonate (cat #55761 Sigma-Aldrich), L-Glutamine (Sigma-Aldrich), HEPES (cat #15630, Invitrogen). The following solution was aliquoted in separate tubes for each transfection type. Transfection complexes were prepared in individual tubes containing a mixture of the transfection agent (Lipofectamine 2000, Invitrogen) and desired DNA vectors in a ratio of 0.4 ug/uL, following the manufacturer's preparation guidelines. Trabecular meshwork cells were obtained from a confluent layer of trypsin-treated 25 $cm^2$ cell culture flask (cat #353109, Becton Dickinson, Franklin Lakes, N.J.) sedimented for 5 minutes at 800 RPM. Cell pellet was then re-suspended in serum free DMEM 1×, (Mediatech) media, thoroughly mixed and finally, equally aliquoted into each respective transfection-complex containing vessel. The reaction was allowed to occur for 45 minutes, after which it was terminated through addition of cell culture media and rat tail collagen (cat #354249, BD, San Jose, Calif.) to initiate gel polymerization. The suspension was gently mixed by aspiration and aspirated into 1 mL single use needle syringe and injected into a borosilicate glass capillary (O.D −1.0 mm, IN.D −0.75 mm) (cat #TW100-6, WPI) to approximately half of its volume. A digital picture snapshot was taken of all capillaries prepared against a blank background with a millimeter scale, repeated at 24 and 48 hours. The hydro-gel containing capillaries were incubated inside a moisture chamber to prevent dehydration in a cell line incubator at 37° C. and 5% $CO_2$. Photographs obtained were analyzed using ImageJ (v.1.43u) measuring between chosen points on the opposite ends of the gel. Amassed length data was statistically analyzed using Microsoft Excel (XP).

Elastic modulus determination: Human donor eyes or corneal buttons were obtained from various eye banks. The ages of the donors ranged from 37 to 80 years. The tissues were maintained in corneal storage medium (Optisol; Chiron Ophthalmics Irvine, Calif.) at 4° C. before they were dissected to remove the TM. The samples were prepared by dissection of the iris and uveal tissue with an ophthalmic knife (World Precision Instrument Inc., Sarasota, Fla.). The human TM was sectioned with a razor blade to provide samples less than 1 cm in length, and the sections were removed from the angle with forceps. The tissue was oriented so that the Schlemm's canal SC side of the JCT was probed and was affixed in the trabecular region with cyanoacrylate glue in the center of a stainless-steel AFM disc. AFM analysis was performed in 1× phosphate-buffered saline (PBS). The average time from donation to analysis was 9±2 days for normal and 10±4 days for glaucomatous samples (Table 1 (FIG. 11)).

To characterize the region of tissue investigated with the AFM, multiple normal corneal buttons were processed for histopathology at various stages of preparation. Donor tissues were processed for routine histology as wedges of intact limbus, wedges of limbus after sharp dissection of uveal tissue, isolated human TM (longitudinal and cross section), and wedges of limbus after HTM isolation. All samples were fixed for 24 to 48 hours and processed routinely, and sections of isolated human TM were oriented for either longitudinal or cross-sectional sampling. After they were embedded, the samples were sectioned at 4 µm and stained with hematoxylin and eosin.

Force curves were acquired with a scanning probe microscope (Nanoscope IIIa Multimode; Veeco Instruments, Inc., Santa Barbara, Calif.). The samples were transferred to the AFM without drying and placed in a commercially available liquid cell (Veeco Instruments, Inc.). Silicon nitride cantilevers with a borosilicate sphere as the tip (1 µm radius; Novascan Technologies, Inc., Ames, Iowa) were used to sample a large area of the human TM. The nominal spring constant of the cantilevers was 0.06 N/m. Force curves were obtained on at least 10 different locations, at either random locations on the sample or in a line with each measurement location separated by approximately 50 µm. We acquired data at random locations with each force curve taken at a rate of 2 µm/s and a minimum of three force curves at each location. Data exhibiting nonlinear behavior was not included in the analyses. Data where a large adhesion with the surface was experienced was also excluded from analysis. A minimum of three locations were used to calculate the mean elastic modulus. Analyses of data was performed utilizing the procedure described by Last et al., 2011.

Elastic modulus determination was performed using atomic force microscopy (AFM) following established protocols (Russell, P. and Johnson, M. Invest Ophthalmol Vis Sci. 53: 117, 2012). Utilized were n=6 donors in each group (control and POAG). All donor eyes that were enucleated within a maximum of six hours and obtained within 7 days of enucleation were acceptable. Prior to measurements TM tissues were carefully dissected and used for elastic modulus determination. Briefly, the petri-dish containing the sample was placed under the polymethylmethacrylate (PMMA) block containing the AFM cantilever. An AFM borosilicate glass particle cantilever tip (2 um tip radius, 0.06N/m spring constant, Novascan Technologies, Ames, Iowa) was positioned onto the sample using a piezoelectric mechanism (60 µm maximal expansion, P-841.40, Physik Instrumente, Germany) until the tip touched the surface of the tissue. The cantilever was observed using the microscope objective connected to the camera beneath the sample. All experiments were performed at room temperature. The Young's modulus was determined using custom developed Matlab software utilizing the Hertz model for a spherical indenter. Average and standard deviation was calculated using acquired data.

Topical application of lipids and measurement of IOP: The lipids were topically applied as 1 µl drops with 10 pmole lipids. Pressure was measured with a tonolab (Colonial Medical Supplies, N.H.) or with an assembled cannulation device, used in our laboratory. An initial assessment had utilized 10% DMSO as vehicle. However, all data reported here utilized 5% DMSO.

Example 2

Examples of Lipid Species That Modulate or Reduce IOP

Phosphatidylcholines:
PC(22: 1(11 Z)/22:6(4Z,7Z, 10Z, 13Z, 16Z, 19Z)) ; 1-(11 Z-docosenoyl)-2-(4Z,7Z, 10Z, 13Z, 16Z, 19Zdocosahexaenoyl)-glycero-3-phosphocholine; CS2HgoNOaP
PC(12:0/14: 1 (9Z))
PC(13:0/20:5(5Z,SZ, 11 Z, 14Z, 17Z))
PC(17: 1(9Z)/22:6(4Z, 7Z, 1 OZ, 13Z, 16Z, 19Z))
PC(0-16:0/17:0)
PC(0-16:0/0-16:0)
PC(P-1S:0/17:2)9Z,12Z))
PC(13:0/20:4)5Z,SZ, 11Z, 14Z))
PC(15:0/1S:2)9Z,12Z))
PC(16:0/20:5(5Z,SZ, 11 Z, 14Z, 17Z))
PC(16: 1 (9Z)/22:6(4Z, 7Z, 1 OZ, 13Z, 16Z, 19Z))
PC(17:0/1S: 1 (9Z))
PC(17: 1 (1OZ)/O:O)
PC(1S: 1 (11Z)/22:6(4Z,7Z, 1 OZ, 13Z, 16Z, 19Z))
PC(1S:3(9Z, 12Z, 15Z)/O:O)
PC(1S:4)9E, 11 E, 13E, 15E)/O:O)
PC(20:3(SZ, 11 Z, 14Z)/O:O)
PC(21 :4)6Z,9Z, 12Z, 15Z)/O:O)
PC(22:6(4Z,7Z,1 OZ, 13Z, 16Z,19Z)/22:6(4Z,7Z, 1 OZ, 13Z, 16Z, 19Z)); 1,2-di-(4Z,7Z,1 OZ, 13Z, 16Z, 19Z-docosahexaenoyl)-sn-glycero-3-phosphocholine; CS2HaoNOaP
PC(25:0/1S:0)
PC(O-12:0/0-12:0)
PC(P-15:0/0:0)

Phosphatidylserines—among those investigated, the most effective in lowering IOP in a mouse model:
PS(1S:3(6Z,9Z, 12Z)/20:5(5Z,SZ, 11 Z, 14Z, 17Z)); 1-(6Z, 9Z, 12Z-octadecatrienoyl)-2-(5Z, SZ, 11 Z, 14Z, 17Z-eicosapentaenoyl)-glycero-3-phosphoserine; C44H70NO1OP
PS(14:0/0:0)
PS(17:0/0:0)
PS(14:0/12:0)
PS(P-16:0/14:1 (9Z))
PS(0-16:0/15:0)
PS(15:0/22:0)
PS(19:0/21:0)

PS(20:0/22:4)7Z,1 OZ, 13Z, 16Z))
PS(20:2)11Z, 14Z)/22:6(4Z,7Z, 1 OZ, 13Z, 16Z, 19Z));
1-(11Z, 14Z-eicosadienoyl)-2-(4Z,7Z, 1 OZ,13Z, 16Z, 19Z-docosahexaenoyl)-glycero-3-phosphoserine; C48H78N01QP
PS(22:6(4Z,7Z,1 OZ, 13Z, 16Z, 19Z)/20:5(5Z,8Z, 11Z, 14Z, 17Z)); 1-(4Z,7Z,1 OZ, 13Z, 16Z, 19Zdocosahexaenoyl)-2-(5Z,8Z, 11 Z, 14Z, 17Z-eicosapentaenoyl)-glycero-3-phosphoserine; C48H72N01QP
PS(0-16:0/12:0)
Phosphatidylethanolamines:
PE(18: 1 (9E)/18: 1 (9E))
PE(18:3(6Z,9Z, 12Z)/22:6(4Z,7Z, 1 OZ, 13Z, 16Z, 19Z))

Example 3

Electron Microscopy and Related Methods Demonstrate Higher Levels of PS in Non-glaucomatous vs. Glaucomatous AH Electron Microscopy: The human aqueous humor from control and POAG donors was centrifuged at 4° C. for 15,000 rpm for 15 minutes. The upper aqueous phase and the lower pellets were separately floated or submerged on an electron microscope (EM) copper or nickel grid. The staining was performed using OsO4 vapors or with 2% phosphotungstic acid (PTA) or both following previously published methods with minor modifications. Briefly, nickel grids were floated for 10 minutes on a drop of upper phase or lower aqueous humor pellet. The copper grids were submerged for 20 minutes in the lower phase pellet of aqueous humor. The nickel grids were exposed to 4% aqueous OsO4 vapors for 30 minutes. The copper grids floated on 0.1 M phosphate buffer, drained and subjected to 4% aqueous OsO4 and 2% phosphotungstic acid as with nickel grids. A subset of grids were also fixed with 2% glutaraldehyde for 5 min, rinsed with 0.1 M phosphate buffer and stained with 4% uranyl acetate for 8 minutes. All grids were examined with a Philips CM10 electron microscope. Magnifications for electron microscopy 300,000× or 200,000× as noted in the individual cases.

Figure 12:
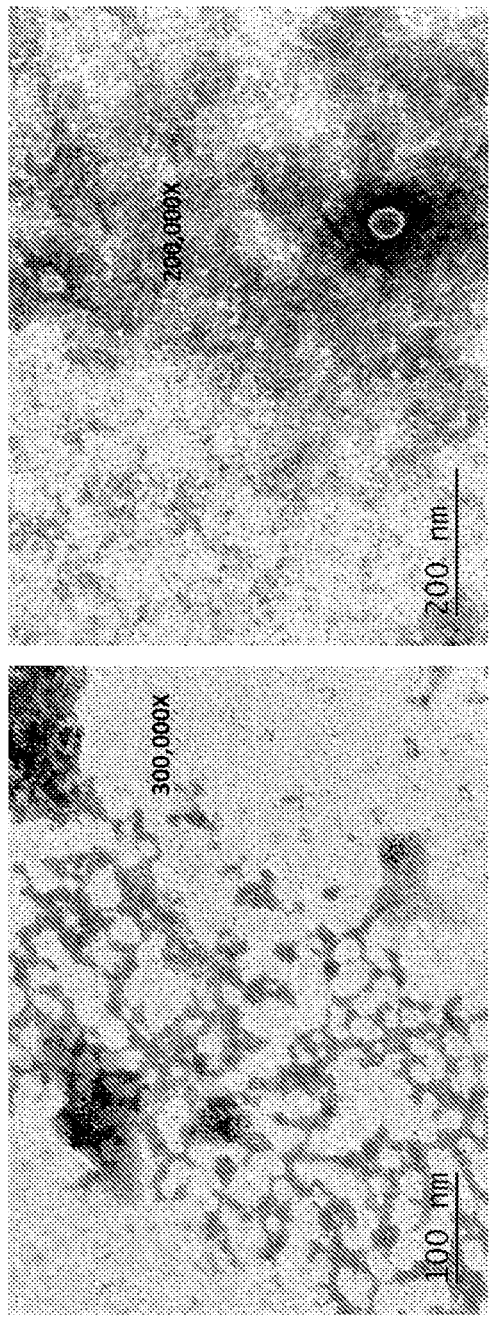
FIG. 12 contains two electron microscopic pictures of control and POAG aqueous humor. Aqueous humor (AH) derived from Control (53 yr old) and POAG (66 yr old) were subjected to centrifugation and lower phase (pellet) was subjected to electron microscopy on a copper grid. The conditions were 0.1 M phosphate buffer and 2% phosphotungstic acid (PAT). The grid was subjected to 4% aqueous OsO4 vapors in 2%PTA.

Results: The control but not POAG aqueous humor showed lipid vesicle like structures which is consistent with the mass spectrometric aqueous humor analyses showing higher levels of phosphatidylserine (PS) in normal controls compared to POAG patients. These results are shown in FIG. 12.

Example 4

Compositions of the Disclosure Reduce IOP in Primates In Vivo

Experimental design: The IOP-reducing activity of six lipids was tested in the eyes of cynomolgus monkeys (n=4 animals for each lipid). Baseline slit lamp biomicroscopic examination (SLE) and IOP for each group of animals was measured prior to topical application of lipids. The SLE and IOP were then measured at 3-6 hours posttreatment. One eye of each monkey received topical application with the lipid suspended in vehicle (1% dimethylsulfoxide (DMSO)), and the contralateral eye was treated with vehicle only. All topical applications contained 10 picomole of lipid (except C17S1P, which was 50 nM). The selected range was found to occur naturally in healthy eyes in normal individuals, as well as in the normotensive mouse eyes. The IOP was measured using a minified Goldmann applanation tonometer.

Results: The results are summarized in FIG. 13. Lyso-PS, C17S1P and PS(18:1) reduced IOP significantly in the normotensive monkeys without additional adverse side effects or toxicity.

Other Embodiments

Any improvement may be made in part or all of the compositions, kits, and method steps. All references, including publications, patent applications, and patents, cited herein are hereby incorporated by reference. The use of any and all examples, or exemplary language (e.g., "such as") provided herein, is intended to illuminate the invention and does not pose a limitation on the scope of the invention unless otherwise claimed. Any statement herein as to the nature or benefits of the invention or of the preferred embodiments is not intended to be limiting, and the appended claims should not be deemed to be limited by such statements. More generally, no language in the specification should be construed as indicating any non-claimed element as being essential to the practice of the invention. This invention includes all modifications and equivalents of the subject matter recited in the claims appended hereto as permitted by applicable law. Moreover, any combination of the above-described elements in all possible variations thereof is encompassed by the invention unless otherwise indicated herein or otherwise clearly contraindicated by context.

What is claimed is:

1. A method of reducing intraocular pressure in a subject, the method comprising administering to the subject a composition comprising a pharmaceutically acceptable vehicle and at least one lipid selected from the group consisting of: PC(12:0/14:1(9Z)), PE(18:0/18:0), PS(14:0/0:0), PS(18:0/0:0), PS18:0 Lyso-PS, PS: 18:1, PI(12:0/17:2(9Z, 12Z)), PI(18:0/20:4(5Z,8Z,11Z,14Z)), C18:1 Dihydroceramide (d18:0/18:1(9Z)) (N-oleoyl-D-erythrosphinganine), Cer(d18:1/26:1(17Z)), SM(d16:1/25:0), Sphinganine, and C17 Sphinganine-1-phosphate in a therapeutically effective amount for promoting aqueous outflow through trabecular meshwork (TM) in at least one eye of the subject and reducing intraocular pressure in the subject.

2. The method of claim 1, wherein the subject has glaucoma and administration of the composition reduces or prevents vision loss in the subject.

3. The method of claim 2, wherein the glaucoma is primary open angle glaucoma or normal tension glaucoma.

4. The method of claim 1, wherein the composition is formulated for topical administration and is administered to the patient topically at least once per day.

5. The method of claim 1, wherein the composition comprises two or more lipids selected from the group consisting of: PC(12:0/14:1(9Z)), PE(18:0/18:0), PS(14:0/0:0), PS(18:0/0:0), PS18:0 Lyso-PS, PS: 18:1, PI(12:0/17:2(9Z,12Z)), PI(18:0/20:4(5Z,8Z,11Z,14Z)), C18:1 Dihydroceramide (d18:0/18:1(9Z)) (N-oleoyl-D-erythrosphinganine), Cer(d18:1/26:1(17Z)), SM(d16:1/25:0), Sphinganine, and C17 Sphinganine-1-phosphate.

6. The method of claim 1, wherein the composition comprises two or more analogs of two or more lipids selected from the group consisting of: PC(12:0/14:1(9Z)), PE(18:0/18:0), PS(14:0/0:0), PS(18:0/0:0), PS18:0 Lyso-PS, PS: 18:1, PI(12:0/17:2(9Z,12Z)), PI(18:0/20:4(5Z,8Z,11Z, 14Z)), C18:1 Dihydroceramide (d18:0/18:1(9Z)) (N-oleoyl-D-erythro-sphinganine), Cer(d18:1/26:1(17Z)), SM(d16:1/25:0), Sphinganine, and C17 Sphinganine-1-phosphate.

7. The method of claim 1, wherein the composition further comprises a prostaglandin or prostaglandin analog.

8. The method of claim 1, further comprising administering a second composition comprising a prostaglandin or prostaglandin analog to the subject.

9. The method of claim 8, wherein the composition comprising the at least one lipid and the second composition are administered to the subject concomitantly or at first and second time points.

* * * * *